US010729660B2

(12) United States Patent
Catalucci et al.

(10) Patent No.: US 10,729,660 B2
(45) Date of Patent: Aug. 4, 2020

(54) PRODUCTS FOR THE DELIVERY OF THERAPEUTIC/DIAGNOSTIC COMPOUNDS TO THE HEART

(71) Applicants: CONSIGLIO NAZIONALE DELLE RICERCHE, Rome (IT); ISTITUTO NAZIONALE ASSICURAZIONE CONTRO GLI INFORTUNI SUL LAVORO, Rome (IT)

(72) Inventors: Daniele Catalucci, Segrate (IT); Michele Miragoli, Cremona (IT); Michele Iafisco, Bologna (IT); Anna Tampieri, Faenza (IT)

(73) Assignees: CONSIGLIO NAZIONALE DELLE RICHERCHE ISTITUTO NAZIONALE PER L'ASSICURAZIONE, Rome (IT); CONTRO GLI INFORTUNI SUL LAVORO, Rome (IT)

(*) Notice: Subject to any disclaimer, the term of this patent is extended or adjusted under 35 U.S.C. 154(b) by 0 days.

(21) Appl. No.: 15/538,663

(22) PCT Filed: Dec. 22, 2015

(86) PCT No.: PCT/EP2015/080991

§ 371 (c)(1),
(2) Date: Jun. 22, 2017

(87) PCT Pub. No.: WO2016/102576

PCT Pub. Date: Jun. 30, 2016

(65) Prior Publication Data

US 2017/0348245 A1 Dec. 7, 2017

(30) Foreign Application Priority Data

Dec. 22, 2014 (IT) .............................. MI2014A2207

(51) Int. Cl.

| | |
|---|---|
| ***A61K 9/51*** | (2006.01) |
| ***A61K 9/14*** | (2006.01) |
| ***A61K 47/69*** | (2017.01) |
| ***A61K 47/52*** | (2017.01) |
| ***A61K 9/00*** | (2006.01) |
| ***A61K 31/7105*** | (2006.01) |
| ***A61K 38/03*** | (2006.01) |
| ***C12N 15/113*** | (2010.01) |

(52) U.S. Cl.

CPC ............ *A61K 9/5115* (2013.01); *A61K 9/007* (2013.01); *A61K 9/143* (2013.01); *A61K 9/5192* (2013.01); *A61K 31/7105* (2013.01); *A61K 38/03* (2013.01); *A61K 47/52* (2017.08); *A61K 47/6929* (2017.08); *C12N 15/113* (2013.01); *C12N 2310/141* (2013.01); *C12N 2320/32* (2013.01)

(58) Field of Classification Search

CPC .... A61K 9/143; A61K 9/5115; A61K 9/5192; A61K 9/007; A61K 38/03; A61K 47/52; A61K 47/692952; A61K 31/7105; C12N 15/113; C12N 2310/141; C12N 2320/32

See application file for complete search history.

(56) References Cited

U.S. PATENT DOCUMENTS

| | | | | |
|---|---|---|---|---|
| 10,105,390 | B2 | 10/2018 | Lopez et al. | |
| 2010/0086601 | A1* | 4/2010 | McDonough ........ | A61K 9/5115 424/489 |
| 2010/0311595 | A1* | 12/2010 | Ryan ...................... | A61K 9/127 504/359 |

(Continued)

FOREIGN PATENT DOCUMENTS

| | | | |
|---|---|---|---|
| WO | 2004/050065 | A1 | 6/2004 |
| WO | WO 2004050065 | A1 * | 6/2004 |
| WO | 2010/085651 | A1 | 7/2010 |

OTHER PUBLICATIONS

Neumann et al., "The Use of Size-Defined DNA-Functionalized Calcium Phosphate Nanoparticles to Minimise Intracellular Calcium Disturbance During Transfection," Biomaterials 30(35):6794-802 (2009).

Graham and Van Der Eb, "A New Technique for the Assay of Infectivity of Human Adenovirus 5 DNA," Virology 52 (2):456-67 (1973).

Lee et al., "Stabilized Calcium Phosphate Nano-Aggregates Using a Dopa-Chitosan Conjugate for Gene Delivery," Int J Pharm 445(1-2):196-202 (2013).

Kakizawa and Kataoka, "Block Copolymer Self-Assembly Into Monodispersive Nanoparticles With Hybrid Core of Antisense DNA and Calcium Phosphate," Langmuir 18(12):4539-4543 (2002).

(Continued)

*Primary Examiner* — Blessing M Fubara
(74) *Attorney, Agent, or Firm* — Pepper Hamilton LLP

(57) ABSTRACT

The invention relates to a process for the preparation of a product comprising one or more nanoparticles of calcium phosphate (CaP-NP) with negative surface charge having a ζ-potential in the range from −41.0 mV to −27.0 mV comprising the steps of: a) maintaining a mixture having a pH in the range from 7 to 10 and comprising an aqueous solution of calcium, an aqueous solution of phosphate and a solution of citrate ions at a temperature in the range from 20° C. to 40° C. for a time in the range from 30 seconds to 10 minutes; b) removing non-reacted ions from the solution of step a), thus obtaining a suspension of one or more nanoparticles of calcium phosphate (CaP-NP); c) recovering the product of one or more nanoparticles of calcium phosphate (CaP-NP) from the suspension of step b). In an advantageous embodiment, the process of the invention provides, in the mixture of step a), also an aqueous solution of one or more therapeutic/diagnostic compounds. The product of the invention may be used as a vehicle for one or more diagnostic/therapeutic compounds for the treatment of cardiovascular diseases through inhalation administration.

24 Claims, 16 Drawing Sheets

(56) References Cited

U.S. PATENT DOCUMENTS

2011/0059889 A1* 3/2011 Mezo .................... C07K 7/06
514/6.9
2013/0267537 A1* 10/2013 Morgan ............... C07D 207/14
514/254.03

OTHER PUBLICATIONS

Miragoli et al., "Functional Interaction Between Charged Nanoparticles and Cardiac Tissue: A New Paradigm for Cardiac Arrhythmia?," Nanomedicine (Lond) 8(5):725-737 (2013).
Li et al., "Calcium Phosphate Nanoparticles With an Asymmetric Lipid Bilayer Coating for siRNA Delivery to the Tumor," J Control Release 158(1):108-14 (2012).
Giger et al., "Gene Delivery with Bisphosphonate-Stabilized Calcium Phosphate Nanoparticles," J Control Release 150(1):87-93 (2011).
Sokolova and Epple, "Inorganic Nanoparticles as Carriers of Nucleic Acids Into Cells," Angew Chem Int Ed Engl 47(8):1382-95 (2008).
International Search Report and Written Opinion for corresponding Application No. PCT/EP2015/080991 (dated Jun. 6, 2016).
Morgan et al., "Encapsulation of Organic Molecules in Calcium Phosphate Nanocomposite Particles for Intracellular Imaging and Drug Delivery," Nano Lett. 8(12):4108-4115 (2008).

* cited by examiner

PRODUCTS FOR THE DELIVERY OF THERAPEUTIC/DIAGNOSTIC COMPOUNDS TO THE HEART

This application is a national stage application under 35 U.S.C. § 371 of PCT Application No. PCT/EP2015/080991, filed 22 Dec. 2015, which claims priority of Italy Application No. MI2014A002207, filed 22 Dec. 2014, which are hereby incorporated by reference in their entirety.

FIELD OF THE INVENTION

The present invention is an innovative therapeutic strategy for the treatment of heart diseases. Specifically, the invention relates to a process for the preparation of a product comprising one or more particles of calcium phosphate encapsulating one or more diagnostic/therapeutic compounds and a product obtained by such a process. The invention also relates to the use of the product of the invention in the treatment of heart diseases through inhalation administration.

PRIOR ART

Recent studies in medicine have been focused on designing and developing multifunctional nanoparticles (NPs) for specific delivery of drug to a selected organ for the purpose of defining a selective and effective therapeutic approach for the treatment of certain pathological conditions. However, several critical issues still limit the pharmacological application thereof, such as i) the physicochemical nature of the nanomaterials used, their biodegradability, biocompatibility and intrinsic potential cytotoxicity; ii) the effectiveness of administration; iii) the non-selectivity of tissue-specific delivery, which is associated with the onset of side effects; iv) uncontrolled drug release in the bloodstream; v) slow cell dissolution/accumulation; vi) low efficiency in crossing biological barriers. The development of appropriate NPs which, through the definition of an appropriate route of administration, can selectively reach the organ of interest is therefore still critical.

Materials based on calcium phosphate (CaP) are widely used for various biomedical applications due to their biocompatibility and biodegradability. Transfection with CaP-based materials has been used to release genes to different cell types in vitro for over 40 years (Graham, F. L.; Erb, A. J. V. d. A new technique for the assay of infectivity of human adenovirus 5 DNA. Virology, 1973, 52, 456-467; V. Sokolova, M. Epple. Inorganic nanoparticles as carriers of nucleic acids into cells. Angew Chem Int Ed Engl, 47 (8) (2008), pp. 1382-1395). The general method consists in encapsulating genes in a precipitate that forms spontaneously after mixing suitable concentrations of calcium and phosphate ions at certain pH values (higher than 7). This method has many advantages such as: ease of production, low costs and high efficiency in binding nucleotides and nucleic acids. Moreover, CaP based materials are pH-sensitive stability thus providing rapid dissolution in an acidic environment (i.e. endosomes, lysosomes). The complete dissolution of CaP in its ionic constituents prevents undesirable material accumulation in cells and tissues, a drawback often encountered with other inorganic and metallic compounds. In this way, CaP particles can selectively and safely release the agent incorporated therein only after cellular internalization.

However, the biggest problem in producing CaP particles is their tendency to aggregation and growth that causes serious problems of reproducibility in syntheses and prevents an optimal colloidal stability thereof. These complications have slowed their development and thus their in vitro and in vivo use. In fact, large particles of CaP (on a micrometer scale) may also lead to interferences in the amount of intracellular calcium, with the subsequent death of the cell itself (Neumann, S. et al. The use of size-defined DNA-functionalized calcium phosphate nanoparticles to minimize intracellular calcium disturbance during transfection. Biomaterials, 2009, 30 (35), 6794-802). Therefore, it is of great interest to succeed in preparing NPs of CaP that are able to deliver nucleic acids or other compounds, protecting them from the external environment and so as to prevent the premature release or degradation thereof. In order to stabilize NPs of CaP preventing the uncontrolled growth thereof and be able to conjugate the therapeutic agent, coatings with synthetic polymeric materials have been used (polyethylene glycol (PEG) (Kakizawa, Y.; Kataoka, K. Block Copolymer Self-Assembly into Monodispersive Nanoparticles with Hybrid Core of Antisense DNA and Calcium Phosphate. Langmuir, 2002, 18 (12), 4539-4543); polyethylenimine (PEI) (T. Devarasu, et al. Potent calcium phosphate nanoparticle surface coating for in vitro and in vivo siRNA delivery: a step toward multifunctional nanovectors); chitosan (Giger, E. V. et al. Gene delivery with bisphosphonatestabilized calcium phosphate nanoparticles. Journal of controlled release: official journal of the Controlled Release Society, 2011, 150 (1), 87-93), bisphosphonates (Lee, K. et al. Stabilized calcium phosphate nano-aggregates using a dopachitosan conjugate for gene delivery. International journal of pharmaceutics, 2013, 445 (1-2), 196-202) or lipids (Li, J.; Yang, Y.; Huang, L. Calcium phosphate nanoparticles with an asymmetric lipid bilayer coating for siRNA delivery to the tumor. Journal of controlled release: official journal of the Controlled Release Society, 2012, 158 (1), 108-14). However, such synthetic polymeric materials are usually not fully biodegradable and may cause allergic reactions.

In the treatment of tumors, CaP-based NPs were prepared and coated with polyethylenimine for the conjugation of long chain of microRNAs (Hyosook Jung et al "Long chain microRNA conjugates in calcium phosphate nanoparticles for efficient formulation and delivery", Arch. Pharm. Research, 2014). These conjugates were released successfully in vitro in prostate cancer cells. Cardiovascular diseases are the leading cause of death and attempts for their treatment have also been made through the use of NPs. However, the development and use of efficient NPs for the therapeutic treatment of cardiovascular diseases is still in its start. In fact, only dendrimers, liposomes or NPs based on non-biomimetic synthetic polymers have been investigated so far for the in vivo delivery of various therapeutic molecules to myocardial cells. This limitation is due to several concerns that have hindered NP translation to the clinic, such as: i) low biodegradability and biocompatibility; ii) toxic byproducts; iii) poor encapsulation efficiency; iv) poor storage stability; v) uncontrolled drug release in the bloodstream; vi) limited cell-target specificity; vii) slow cell dissolution/accumulation; viii) poor efficiency of systemic administration approaches; ix) low efficiency in crossing biological barriers. Therefore, new approaches for safe, efficient, and cardiac-specific delivery of therapeutic drugs are strongly required. Recently (Michele Miragoli et al., "Functional interaction between charges nanoparticles and cardiac tissue: a new paradigm for cardiac arrhythmia?" Nanomedicine (2013)8(5), 725-737), it was described how polystyrene latex NPs (50 nm dimensions) can, depending on their surface electrical charge, interact with polarized cardiac cells (cardiomyocytes). In particular, it was shown how the use of NPs with negative surface charge facilitates the entry of the NP itself within the cardiomyocyte through the formation of transient nanopores compatible with the cell viability, in contrast to the apoptotic response and subsequent cell death triggered by the use of positively charged NPs. However, despite the partial effectiveness in in vitro administrations, the potential of these negatively charged polystyrene latex NPs as potential drug carriers is drastically limited for chronic administrations, due to major side effects, such as changes in the electrophysiological profile and sensitization to arrhythmia, thus being a considerable limit for a potential therapeutic use thereof in vivo.

The object of the present invention is to provide an approach based on nanoparticles of calcium phosphate (CaP-NPs) for the treatment of heart diseases, which does not have the drawbacks of the prior art, among which the alteration of the cardiac electrophysiological profile.

SUMMARY OF THE INVENTION

The inventors of the present invention have surprisingly found a process for the preparation of a product consisting of one or more nanoparticles of calcium phosphate (CaP-NPs) able to encapsulate and/or be surface functionalized with one or more diagnostic/therapeutic which proved able to be a therapeutic approach for the treatment of cardiovascular diseases without causing arrhythmia or change in the electrophysiological profile of cardiac cells and characterized by direct delivery to the myocardium through a non-invasive inhalation administration route. Additionally, other enteral and parenteral administration routes (i.e. intravenous, intraperitoneal, oral, sublingual, rectal, intraocular, topical or transdermal) can be provided. Additionally, when surface functionalized with non-cardiac cell-specific diagnostic/therapeutic compounds, the present invention is intended for the targeting of other tissue other than the heart.

Therefore, the invention relates to a process for the preparation of a product comprising one or more nanoparticles of calcium phosphate (CaP-NP) with a negative surface charge having a ζ-potential in the range from −41.0 mV to −27.0 mV, comprising the steps of:

a) maintaining a mixture having a pH in the range from 7 to 10 and comprising an aqueous solution of calcium, an aqueous solution of phosphate and a solution of citrate ions at a temperature in the range from 20° C. to 40° C. for a time in the range from 30 seconds to 10 minutes;

b) removing non-reacted ions from the obtained solution of step a), thus obtaining a suspension of one or more nanoparticles of calcium phosphate (CaP-NP);

c) recovering the product of one or more nanoparticles of calcium phosphate (CaP-NP) from the suspension of step b).

The process of the invention allows obtaining a product made of one or more CaP-NP with ζ-potential in the range from −41.0 mV to −27.0 mV and having a splitting factor (SF) of at most 1.76, being said one or more CaP-NP able to enter into cardiac cells and not causing the alteration of the cardiac electrophysiological profile. The product of the invention has proved to be advantageous in the form of nanoparticles with a spheroidal morphology.

In a preferred and advantageous aspect of the invention, the process of the invention comprises adding, in step a), an aqueous solution of one or more therapeutic/diagnostic compounds.

Surprisingly and in the preferred process of the invention, the product of the invention obtainable according to the preferred and advantageous aspect of the invention consists of one or more nanoparticles of calcium phosphate (CaP-NP) encapsulating one or more diagnostic/therapeutic compounds. The product of the invention also encapsulating one or more diagnostic/therapeutic compounds has surprisingly proved to consist of one or more negatively charged CaP-NP with ζ-potential in the range from −41.0 mV to −27.0 mV and with average mean hydrodynamic diameter (measured as Z-average) in the range from 150 to 231 nm. The product of the invention has proved to be advantageous in the form of NP with a spheroidal morphology.

Advantageously, therefore, the invention provides for adding to the mixture of step a) a solution of one or more therapeutic/diagnostic compounds. The invention with the addition of the solution of one or more diagnostic/therapeutic compounds allows obtaining NP with defined dimensions and charge with one or more diagnostic/therapeutic compounds encapsulated therein.

Therefore, the inventors have surprisingly found a low temperature of formation of the NP encapsulating one or more diagnostic/therapeutic compounds which ensures the instant formation of CaP at a low crystallinity, similar as crystallographic structure to an amorphous CaP and of dimensions in the range from 150 to 231 nm. Without being bound to any theory, the inventors of the present invention believe that the selection of temperature and time conditions, as well as the presence of citrate ion, which is a more "bio-friendly" stabilizing agent compared to those used in the prior art, have allowed the CaP-NP encapsulating one or more diagnostic/therapeutic compounds to be stabilized, especially owing to the citrate ion of the mixture that, by binding on the surface, prevents further growth thereof and makes them stable at a colloidal level. In addition, the presence of citrate on the surface, as will appear in the experimental part, is able to make the surface of CaP-NP negatively charged and shift the surface potential thereof to broadly negative values able to make them stable at a colloidal level. Moreover, the CaP-NP obtainable with the process of the invention proved to have low crystallinity by having a splitting factor (SF) of at most 1.76, and allowed encapsulating/surface-functionalizing larger amounts of diagnostic/therapeutic compounds. According to the inventors, in fact, the low crystallinity leads to greater structural disorder and thus to a large amount of free ionic sites able to bind therapeutic/diagnostic compounds. Moreover, the CaP-NP of preferred and advantageous embodiment of the invention was found to have an average mean of hydrodynamic diameter (measured as Z-average) in the range from 150 to 231 nm, which advantageously allows the use thereof in the treatment of heart diseases.

Another advantageous feature of the present invention consists in mixing the therapeutic/diagnostic compound directly during the synthesis of CaP-NPs. Moreover, the low level of crystallinity (expressed as splitting factor (SF) of at most 1.76) obtained by this procedure increases the time of degradability of CaP-NPs, thus favoring a faster release of the therapeutic/diagnostic compound. Moreover, by increasing the level of crystallinity obtained by this procedure decreases the time of degradability of CaP-NPs, thus favoring a slow release of the therapeutic/diagnostic compound.

Another advantageous feature of the present invention consists in possible surface functionalization of the final CaP-NP product, thus favoring distinctive needs of drug-targeting specificity (i.e. binding of an extracellular target for cell-specific guidance and/or receptor activation/inhibition).

In the present invention, the term/definition:

"therapeutic/diagnostic compound(s)" means one or more medical compounds, e.g. nucleic acids, peptide, synthetic compounds or diagnostic probes for release to the organ of interest;

"Z-average" in the range from 150 to 231 nm means the mean hydrodynamic diameter determined by Dynamic Light Scattering (DLS).

"negatively charged CaP-NP with ζ-potential in the range from −27.0 mV to −41.0 mV" means CaP-NP with ζ-potential determined by Electrophoretic Light Scattering (ELS);

"splitting factor (SF)" measures the degree of crystallinity calculated from FT-IR spectra of the NP according to Weiner S. and Bar-Yosef O. (1990). States of preservation of bones from prehistoric sites in the Near East: a survey. Journal of Archaeological Science 17, 187-196.

In another aspect thereof, the invention relates to a product obtainable with the process of the invention for use as vehicle in the treatment of cardiovascular diseases through inhalation administration.

In a further and advantageous aspect thereof, the invention relates to a product obtainable with the process of invention in its preferred and advantageous embodiment with one or more compounds encapsulated in the one or more CaP-NP for use in the treatment of cardiovascular diseases through inhalation administration.

The invention therefore is particularly advantageous in the field of nanomedicine applied to the non-invasive treatment of cardiovascular diseases through inhalation administration.

The inventors of the present invention surprisingly had the intuition to treat cardiovascular diseases with the product of the invention through inhalation administration, which allowed the product of the invention to reach the myocardium through the heart-lung axis. As a consequence and surprisingly, the treatment by inhalation of the product of the invention allowed passing the lung barrier and translocating to blood circulation, thereby entering the pulmonary-heart blood circulation and reaching the heart where it would target cardiac tissue/cells, and interact with and be internalized by polarized cardiomyocytes. This facilitated the release of the therapeutic/diagnostic compound to the myocardium.

Additionally, the invention relates to a product obtainable with the process of invention administrable via other enteral and parenteral administration routes (i.e. intravenous, intraperitoneal, oral, sublingual, rectal, intraocular, topical or transdermal).

The inventors of the present invention also had the intuition of employing calcium phosphate nanoparticles (CaP-NPs) for the encapsulation of compounds to be released to the myocardium. In the study that led to the invention, the CaP-NPs of the process of the invention were surprising in internalizing the compound both in cardiac cells in vitro and the myocardium in vivo. Without being bound to any theory, the inventors established that in the specific application, the CaP-NPs prepared according to the invention and negatively charged were less toxic to cells and facilitated the endocytosis-dependent internalization compatible to the cellular viability. Surprisingly, the presence of a negative charge made the CaP-NP, as such or encapsulating one or more compounds to be released to the myocardium, compatible with the viability of internalization in cells that have hyperpolarized membranes (such as cardiomyocytes) and devoid of side effects such as the onset of arrhythmias. In another aspect of the invention, the CaP-NP can be surface functionalized with targeting ligands (i.e. antibodies, peptide, aptamers) for direct cell-specific binding, internalization, and intracellular release of functional therapeutic drugs to the desired organ, thus improving drug efficacy while minimizing systemic drug exposure and adverse side effects in tissues other than the myocardium.

The invention will now be described in detail and exemplified hereinafter in the experimental part.

I-V curves obtained with ramp protocols in control (left, black: mean+SD; SD shown as a band) and exposed conditions (right, grey) adult ventricular myocytes. (B) Superimposition of the two curves (left) and average difference net membrane current curve (right).

Figure 10:
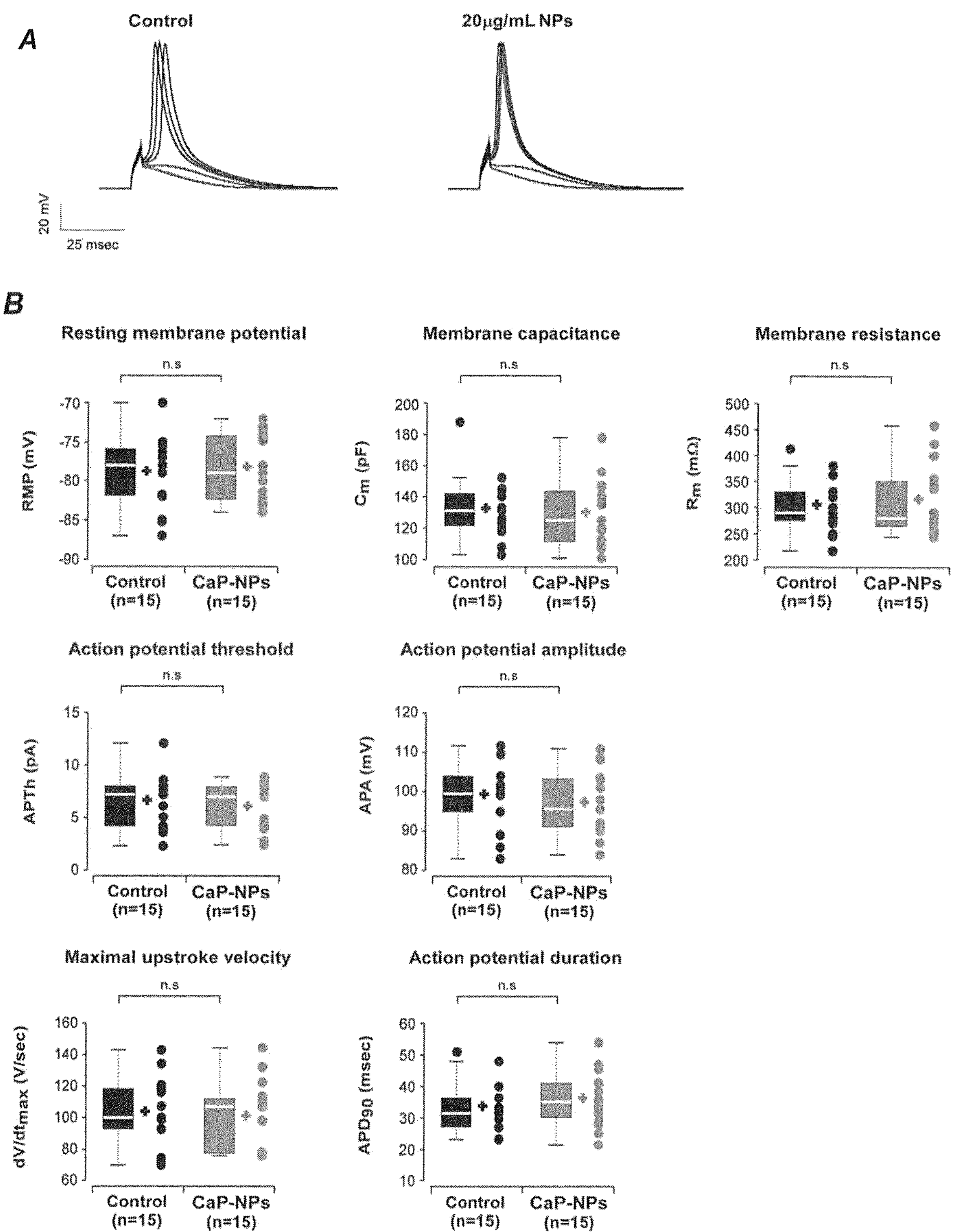

FIG. 10 shows the effects of the CaP-NP on the electrophysiology of ventricular cardiomyocytes of adult mice after 5 hours of exposure of 20 μg/mL CaP-NP. In particular, (A) Representative action potentials recorded in "whole cell current clamp configuration" in control conditions and after application of 20 μg/mL CaP-NP. (B) Effect of the CaP-NP on the membrane potential ($V_m$), membrane capacity ($C_m$) and membrane resistance ($R_m$) (top) of adult cardiomyocytes. Effect of the CaP-NP on the action potential threshold (APth) and AP amplitude (APA) (middle), maximum ascent rate of AP ($dV/dt_{max}$) and AP duration at 90% repolarization ($APD_{90}$) (bottom).

Figure 11:
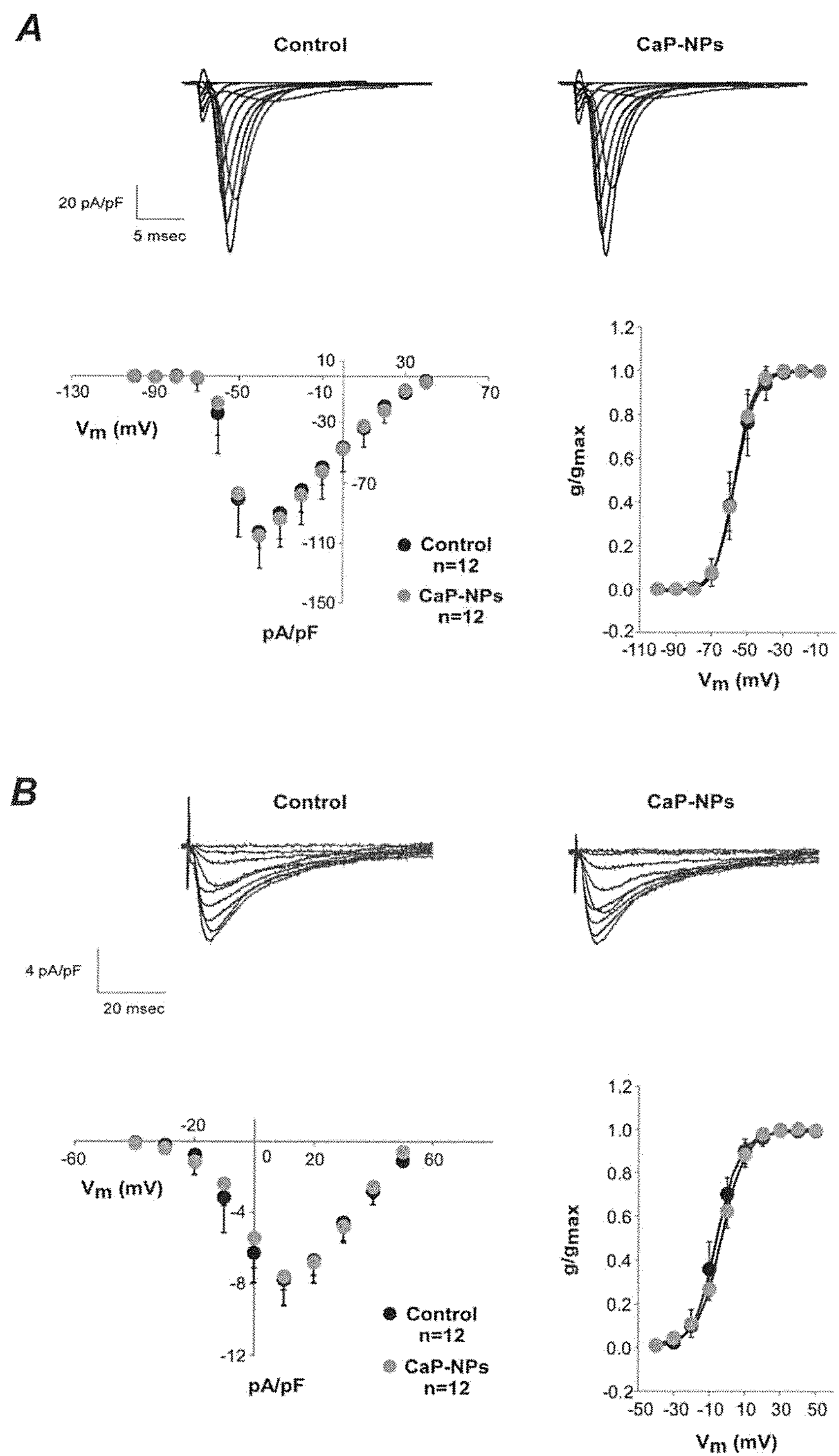

FIG. 11 shows the effects of CaP-NP on the electrophysiology of ventricular cardiomyocytes of adult mice after 5 hours of exposure of 20 μg/mL CaP-NP. In particular, (A) Representative sodium currents recorded in "whole cell voltage clamp configuration" in control conditions and after intervention with 20 μg/mL CaP-NP (top). Overlapping of the mean densities of sodium current peaks as a function of the control potential ("voltage steps" protocols) and voltage-dependence of steady-state activation curves obtained in control conditions (black) and after the application of 20 μg/mL CaP-NP (grey) (bottom). (B) Representative calcium currents recorded in "whole cell voltage clamp configuration" in control conditions and after intervention with 20 μg/mL CaP-NP (top). Overlapping of the mean densities of calcium current peaks as a function of the control potential ("voltage steps" protocols) and voltage-dependence of steady-state activation curves obtained in control conditions (black) and after the application of 20 μg/mL CaP-NPs (grey) (bottom).

Figure 12:
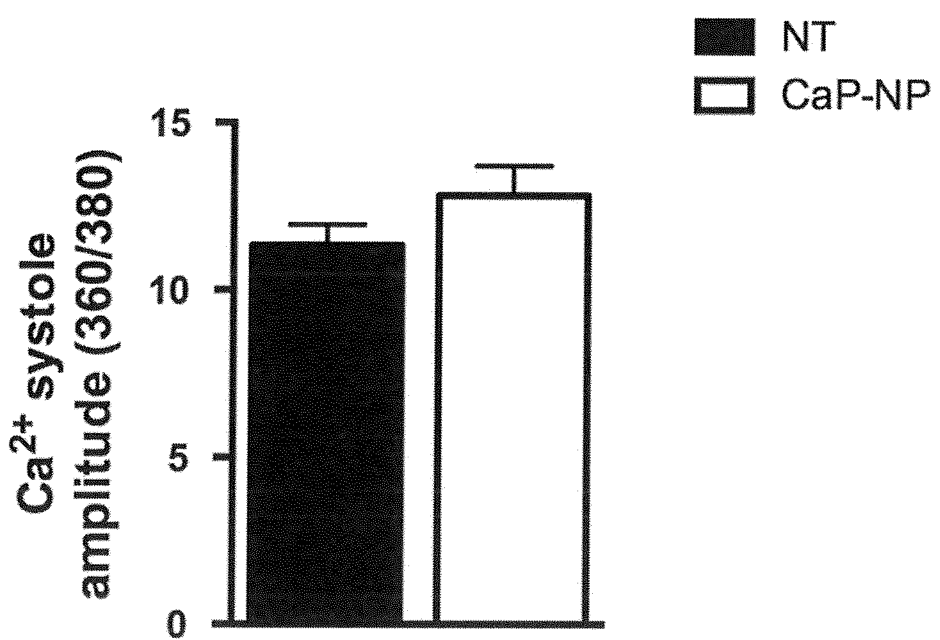

FIG. 12 shows the effects of CaP-NP on the cytosolic calcium levels (calcium transients) of HL-1 cells after exposure for 24 hours to 20 μg/mL CaP-NP. Calcium transients reflect the cyclical variations of the ion in the alternation of systolic/diastolic phases of cardiomyocytes. The cells, analyzed by the system IonOptix, were loaded with the calcium-sensitive fluorophore Fura2.

Figure 13:
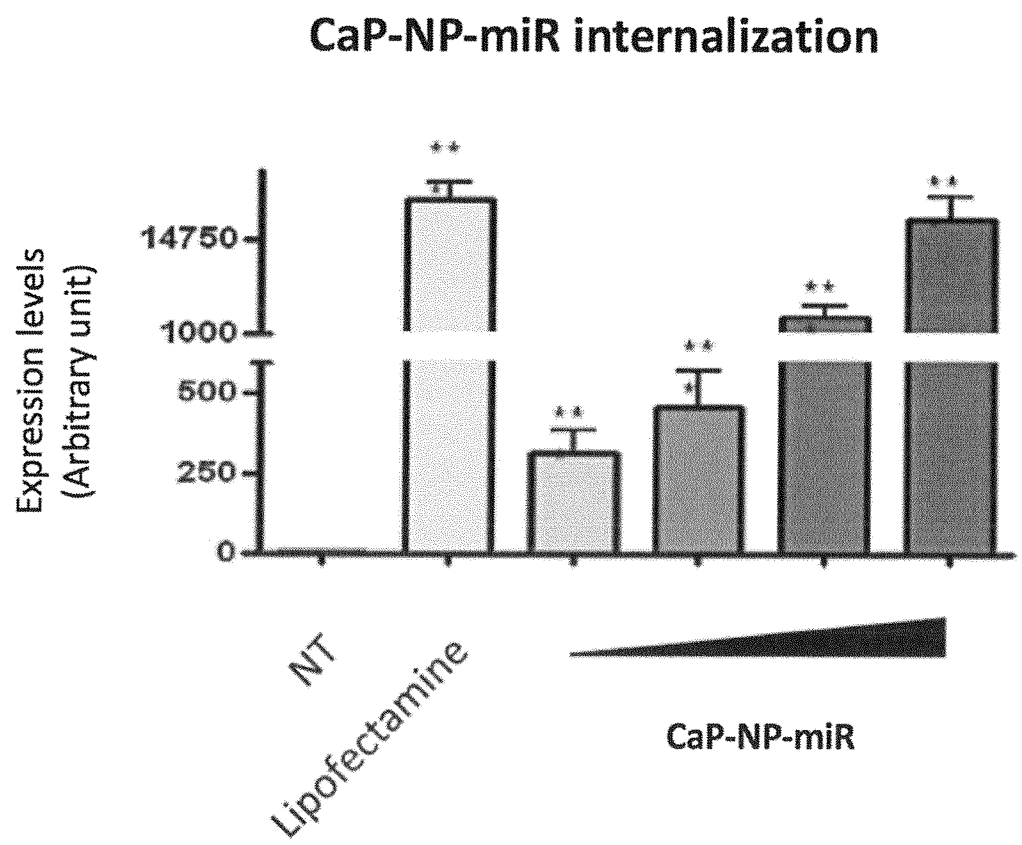

FIG. 13 shows the results of internalization of miR-133 after administration of increasing doses of CaP-NP-miR to HEK293 cells. The quantity of internalized miR-133 was measured by quantitative PCR on total RNA extract. Lipofectamine is a positive control of transfection of miR-133 with liposomes.

Figure 14:
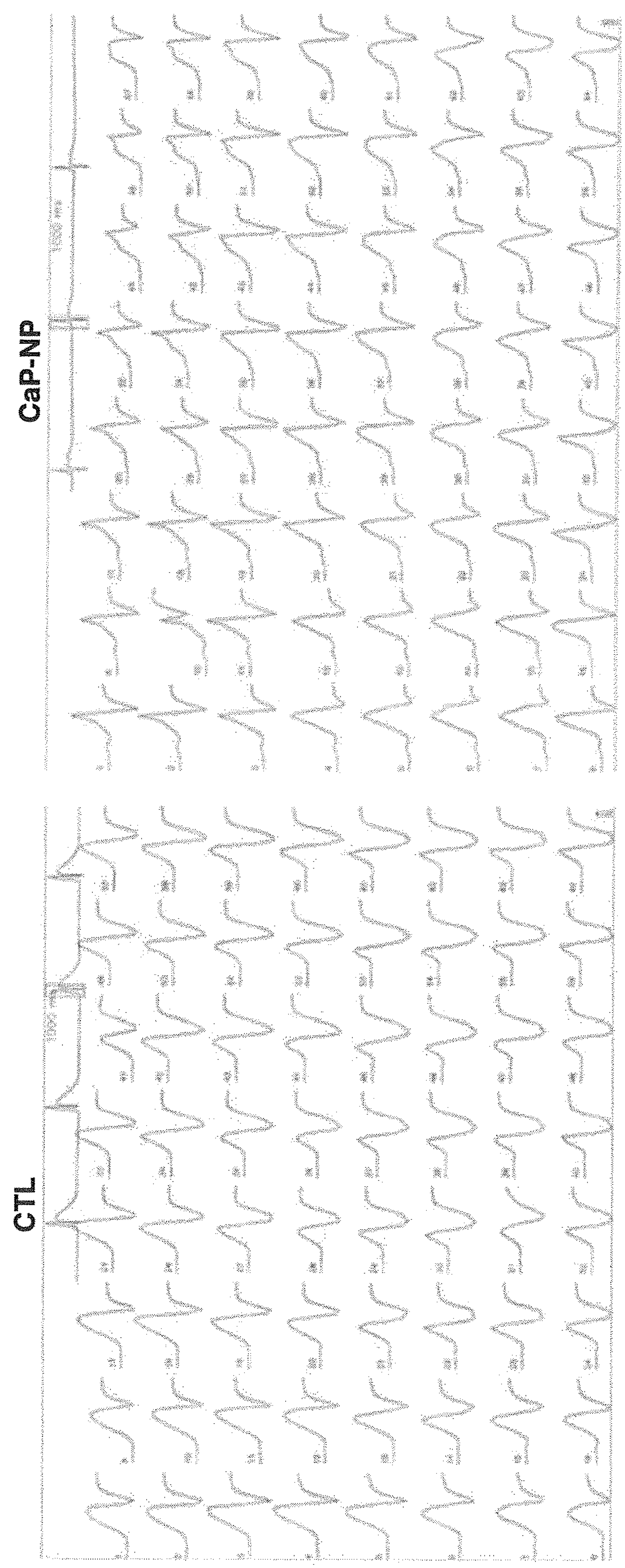

FIG. 14 shows a profile of electrograms performed in adult rats after the tracheal administration of saline alone (Control) or nanoparticles of the invention (CaP-NP).

Figure 15:
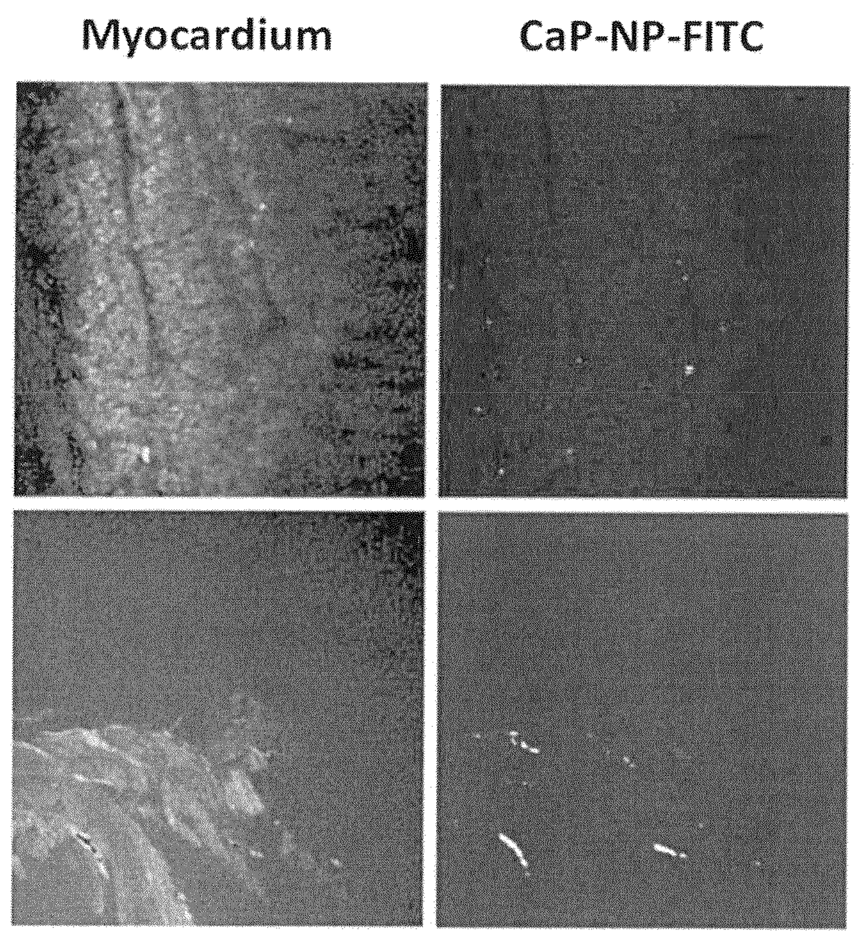

FIG. 15 shows a microscopy analysis on two photons on myocardial tissue of animal treated with CaP-NP-FICT through tracheal instillation. The images show the actual reaching of the ventricular tissue by the CaP-NP-FITC. In the images of the preparation at the bottom, the CaP-NP-FITC are also present inside a vessel.

Figure 16:
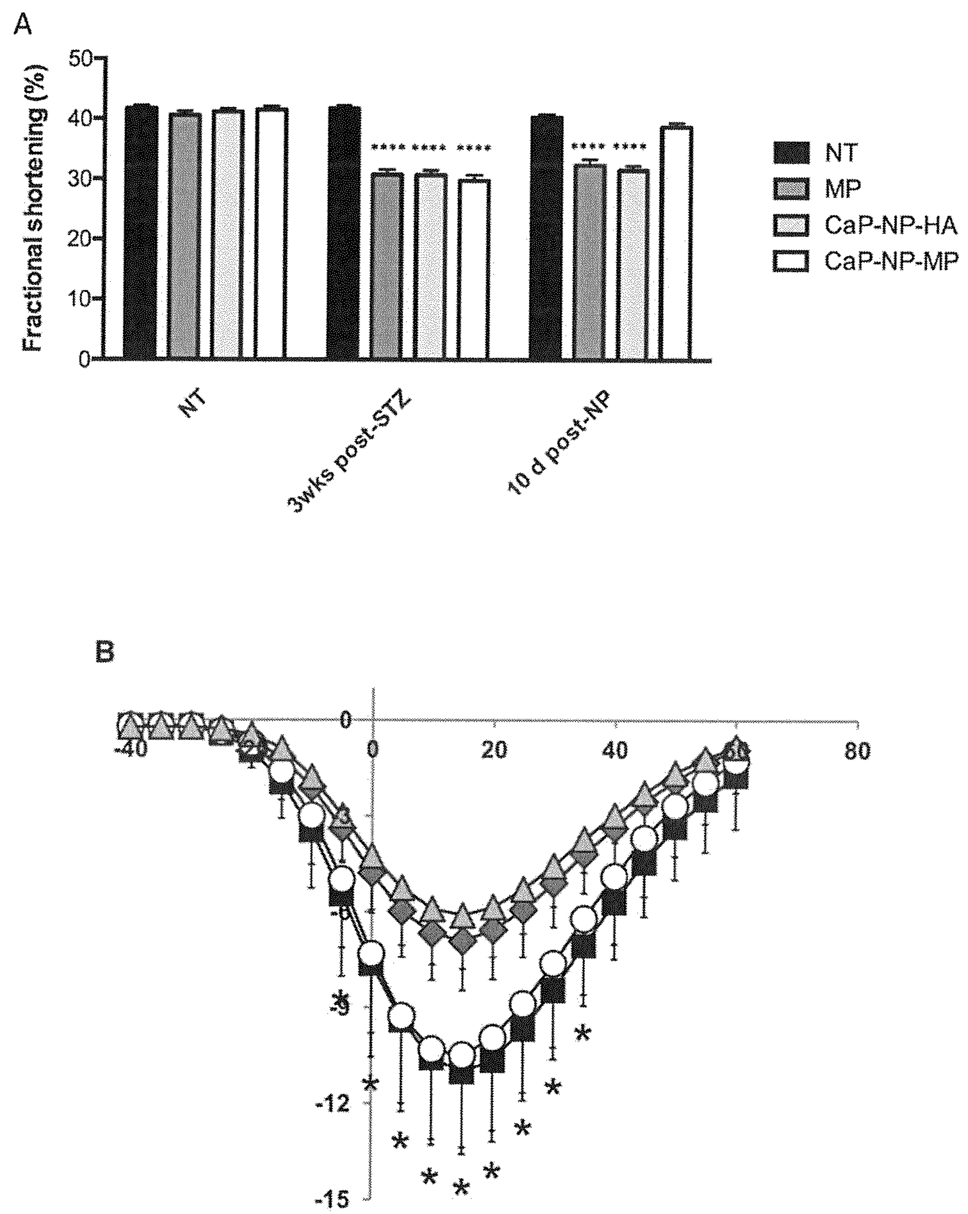

FIG. 16 shows the therapeutic potential of mimetic peptide (MP) described in the PCT application PCT/EP2015/051376 in a mouse model of diabetic cardiomyopathy. MP is a short 9aa peptide that falls in a novel class of positive inotropes. By acting via unconventional mechanisms (i.e. normalization of cell surface density of the voltage-dependent L-Type calcium channel, which is the trigger element leading to the calcium-dependent systolic contraction, and without altering the channel gating properties), MP restores the force of the heartbeat and bypasses the deleterious drawbacks of the previous class of inotropes (i.e. arrhythmogenesis and myocardial oxygen waste). (A) Echo, echocardiography. Fractional shortening (%) as determined by echocardiography in mice treated with streptozotocin (STZ) and MP not encapsulated in CaP-NP (MP), scramble-loaded CaP-NP (CaP-NP-HA) or MP-loaded CaP-NP (CaP-NP-MP). (n=10) (B) $Ca^{2+}$ current measurements in adult cardiomyocytes isolated from treated mice. I/V relationships are shown (n>16). Data are shown as the means±SEM; ****, P<0.0001.

DETAILED DESCRIPTION OF THE INVENTION

Therefore, the invention relates to a process for the preparation of a product comprising one or more nanoparticles of calcium phosphate (CaP-NP) with a negative surface charge having a ζ-potential in the range from −41.0 mV to −27.0 mV, comprising the steps of:

a) maintaining a mixture having a pH in the range from 7 to 10 and comprising an aqueous solution of calcium, an aqueous solution of phosphate and a solution of citrate ions at a temperature in the range from 20° C. to 40° C. for a time in the range from 30 seconds to 10 minutes;

b) removing non-reacted ions from the obtained solution of step a), thus obtaining a suspension of one or more nanoparticles of calcium phosphate (CaP-NP);

c) recovering the product of one or more nanoparticles of calcium phosphate (CaP-NP) from the suspension of step b).

According to the invention, the aqueous solution of calcium in the mixture of step a) is preferably a solution of calcium chloride having a molarity in the range from 20 to 200 mM.

According to the invention, the aqueous solution of phosphate in the mixture of step a) is preferably a solution of $Na_2HPO_4$ having a molarity in the range from 24 to 140 mM.

The temperature of step a) is in the range from 20° C. to 40° C. Preferably, it is in the range from 35 to 40° C., more preferably it is about 37° C.

The maintenance time at a temperature in the range from 20 to 40° C. of the mixture in step a) is in the range from 30 seconds to 10 minutes, preferably it is about 5 minutes.

The solution of citrate ions is preferably an aqueous solution of sodium citrate having a molarity in the range from 40 to 800 mM.

The mixture of step a) has a pH in the range from 7 to 10, more preferably the pH of the mixture is 10.

At the end of step a), the mixture is subjected to a process of removal of non-reacted ions. Preferably, said step is carried out by means of a dialysis membrane. Alternatively, electrophoretic deposition or molecular exclusion chromatography may be used.

When the invention uses a dialysis membrane, it is preferably a cellulose membrane having a cut-off of 3500 Dalton. The removal step b), carried out with a dialysis membrane, occurs preferably for a time from 5 to 24 hours, more preferably for 6 hours.

At the end of the step of removal of non-reacted ions b), a suspension of nanoparticles is obtained that can be subjected to addition of bidistilled water and freeze dried to obtain the CaP-NP of step c). Alternatively, the product of step b) can be freeze-dried to obtain powders.

The process of the invention allows obtaining a product made of one or more CaP-NP with ζ-potential in the range from −41.0 mV to −27.0 mV which is able to enter into cardiac cells and not causing the alteration of the cardiac electrophysiological profile, as will be shown in the experimental part. The product of the invention has proved to be advantageous in the form of NP with a spheroidal morphology. Moreover, the NPs obtainable with the process of the invention proved to have low crystallinity measured as splitting factor of the NP that allowed encapsulating larger amounts of diagnostic/therapeutic compounds. The NP obtainable from process of the invention have low crystallinity comparable to that of an amorphous calcium phosphate (as will be clear from the following experimental part), which in fact leads to greater structural disorder and thus to a large amount of free ionic sites able to bind therapeutic/diagnostic compounds. In a preferred and advantageous aspect of the invention, the process of the invention comprises the addition, in step a), of an aqueous solution of one or more therapeutic/diagnostic compounds. Alternatively, in a further preferred and advantageous aspect of the invention, the process of the invention comprises the addition of a surface functionalization of the final product with one or more therapeutic/diagnostic compounds. Surface functionalization of CaP-NP with diagnostic/therapeutic compounds for example can be carried out by mixing for different times suspensions of CaP-NP with solutions of diagnostic/therapeutic compounds following by washings procedures. Stable binding between diagnostic/therapeutic compounds and CaP-NP can mainly occur through formation of electrostatic interactions.

One or more therapeutic/diagnostic compounds are preferably selected from the groups consisting of nucleic acids, peptides, synthetic compounds and diagnostic probes.

The presence in step a) of the solution of one or more diagnostic/therapeutic compounds of interest allows obtaining, at the end of step c), CaP-NP that have the therapeutic/diagnostic compound(s) encapsulated in the structure.

Therefore, surprisingly, the product of the invention obtainable according to the preferred and advantageous aspect of the invention comprises one or more CaP-NP encapsulating one or more diagnostic/therapeutic compounds and/or comprises one or more surface-functionalized therapeutic/diagnostic compounds. The product of the invention encapsulating one or more diagnostic/therapeutic compounds has surprisingly proved to comprise one or more negatively charged CaP-NP with ζ-potential in the range from −41.0 mV to −27.0 mV and with Z-average in the range from 150 to 231 nm. The product of the invention with the therapeutic/diagnostic compound(s) encapsulated in the structure has proved to be advantageously in the form of CaP-NP with spheroidal morphology.

In another aspect thereof, the invention relates to a product obtainable with the process of the invention for use as vehicle in the treatment of cardiovascular diseases through inhalation administration.

Cardiovascular diseases in the present invention comprise heart failure, decreased myocardial contraction, fibrillation, diabetic cardiomyopathy, dilated cardiomyopathy, genetic diseases (such as Brugada syndrome, Timothy syndrome, or short QT syndrome, muscular dystrophy), cardiac hypertrophy, hypotension, hyperthyroidism, hypothyroidism, acute heart failure, chronic heart failure, myocardial infarction.

In a further and advantageous aspect thereof, the invention relates to a product obtainable with the process of invention in its preferred and advantageous embodiment with one or more compounds encapsulated in the one or more CaP-NP for use in the treatment of cardiovascular diseases through inhalation administration, as explained above and shown in the experimental part. In addition, the invention relates to a product obtainable with the process of invention administrable via other enteral and parenteral administration routes (i.e. intravenous, intraperitoneal, oral, sublingual, rectal, intraocular, topical or transdermal).

EXPERIMENTAL PART

Example 1A. Preparation of the Calcium Phosphate Nanoparticles (CaP-NP) of the Invention A solution containing: 12.5 volumes of a solution of $CaCl_2$ (10-50 mM) and $Na_3$ $(C_6H_5O_7)$ (40-200 mM), 1 volume of a solution of NaOH (0.1-0.5 M) and 12.5 volumes of a solution of $Na_2HPO_4$ (12-60 mM) was prepared and then placed in a water bath at 37° C. for 5 min.

To remove non-reacted reagents, the solution of CaP-NP was subjected to dialysis for 6 hours in a cellulose dialysis membrane having a cutoff of 3500 Dalton and immersed in 400 ml of bidistilled water. The solution was then recovered and stored in a refrigerator at 4° C. The amount of CaP was assessed by freeze-drying of the sample and subsequent weighing of the inorganic residue. The final concentration of the aqueous suspension of CaP was in the range from 60 to 300 μg/ml, as a function of the concentration of reagents.

To prepare the nanoparticles, the synthesis reaction between $Ca^{2+}$ and $PO_4^{3-}$ was carried out at pH 10 adjusting the pH by adding a solution of NaOH (0.1-0.5 M) to prevent the formation of other chemical species. Sodium citrate, present in the initial solution together with calcium and phosphate salts, was the stabilizing agent that allowed the CaP particles to form crystals in a controlled manner (by changing the level of supersaturation of $Ca^{2+}$ and $PO_4^{3-}$).

The NP suspension was analyzed by Dynamic Light Scattering (DLS) revealing a Z-average of the particles in the range of 100-200 nm.

The final concentration of the aqueous suspension of CaP-NP of step b) was in the range from 60 to 300 μg/ml, as a function of the concentration of reagents. The analysis by transmission electron microscopy (TEM) of the product of the invention, i.e. of the CaP-NP, revealed a Z-average of about 50 nm in diameter.

Example 1B: Effects of Citrate Ion and of the Temperature and Time Conditions on the CaP-NP of the Invention In order to assess the essentiality of the presence of citrate ions in step a), the effect of citrate on the dimensions and on the colloidal stability of CaP-NP was assessed in advance by DLS.

Equal volumes of solutions of $Na_2HPO_4$ (24 mM) and $CaCl_2$ (20 mM)+$Na_3Cit$ (20, 40, 80 mM) were mixed directly in the disposable cuvette, kept at 37° C. for 5 minutes and subjected to DLS measurements to assess the size and stability of the CaP-NP precipitate in the absence or in the presence of citrate. Different concentrations of sodium citrate (20, 40, 80 mM) were used.

Figure 1:
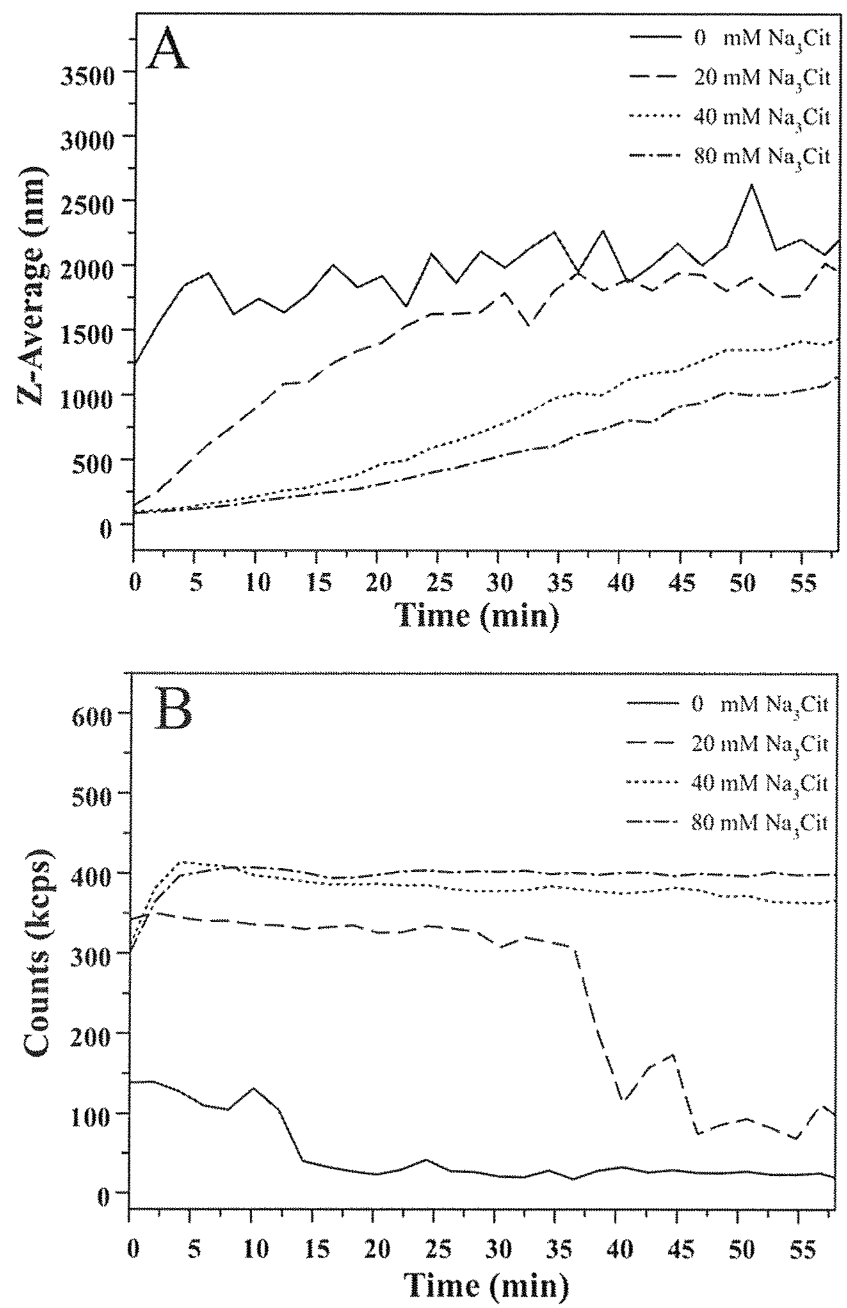
FIG. 1 shows the effects of citrate on the CaP-NP prepared according to the invention. (A, B) Assessment of the colloidal stability and dimensions of CaP-NP synthesized without and with increasing amounts of citrate; (A) Z-average as measure of the mean hydrodynamic diameter and (B) count of the number of photons per second were measured continuously for an hour by DLS.

The hydrodynamic diameter and the number of photons per second were measured for a continuous period of 60 minutes by DLS (FIG. 1A, B).

The data shown in FIG. 1A, where the Z-average of the CaP-NP synthesized in the presence and absence of citrate was measured as a function of the crystallization time, clearly show that the average mean hydrodynamic diameter of the CaP-NP crystallized in the absence of citrate already after few seconds of crystallization was about 2 μm and remained stable for a time of 60 minutes. On the other hand, the Z-average of the CaP-NP synthesized in the presence of citrate after few seconds was significantly smaller than CaP-NP prepared in the absence of citrate (about 100 nm). The average mean hydrodynamic diameter of CaP-NP synthesized in the presence of citrate increased slowly over time than the control sample without citrate, indicating that citrate stabilizes the size of NP and decreases the tendency of CaP-NP to form aggregates. Moreover, these data show that by increasing the amount of citrate during synthesis, the Z-average of CaP-NP increases more slowly and that regardless of the concentration, at low crystallization times the citrate exerts its role of stabilizing the size of NP.

FIG. 1B shows that count of the number of photons per second of the CPC synthesized without citrate or with an amount of 20 mM of citrate decreases over time, so that the amount of material in the cuvette is reduced following its deposit on the bottom. On the other hand, the number of photons detected in the case of CaP-NP synthesized in the presence of an amount of citrate equal to 40 and 80 mM remained stable over time, indicating the excellent colloidal stability of the CaP-NP synthesized in this way. In conclusion, the CaP-NP crystallized in the presence of citrate showed better dimensional and colloidal stability, so the presence of citrate was essential to the stability of the particles.

After assessing the effect of citrate, the optimum crystallization time was assessed. The samples of CaP-NP crystallized in the presence of 80 mM of citrate were prepared at different crystallization times (i.e. 5, 10, 20 and 60 minutes). The reaction products were washed three times with water by centrifugation at 5000 RPM (3.689×g) for 10 minutes and were characterized by DLS, Fourier transform infrared spectroscopy (FTIR) and transmission electron microscopy (TEM). The amount of CaP-NP was evaluated by weighing the inorganic residue after washing and freeze-drying.

The FTIR spectra (FIG. 2) of the CaP-NP synthesized at different times were recorded to assess the chemical structure of the particles. In all cases, the bands typical of CaP were highlighted. In particular, it is possible to see the bands due to the major functional groups present in this structure, such as: 2 bands at about 1040 $cm^{-1}$ and 1100 $cm^{-1}$ due to stretching vibrations of the phosphates; two peaks at 603 $cm^{-1}$ and 560 $cm^{-1}$ attributable to the bending vibrations of the phosphates; two small bands around 1450 $cm^{-1}$ attributable to the stretching vibrations of the carbonate ions. Since the CaP-NP were prepared in an uncontrolled atmosphere, carbonate ions may spontaneously enter in the crystalline structure of the material. This phenomenon is commonly seen also in biological apatites. In all materials, a more intense band is evident at about 1600 $cm^{-1}$ attributable to the stretching vibration of the carboxyl group of citrate. In this way, the actual presence of citrate bound on the surface of the CaP may be confirmed. As the crystallization time increased, a clear transformation was observed from a material with a low long-range order similar to an amorphous material to a more crystalline one.

As the crystallization time increased, the Z-average of CaP-NP increased up to reaching the value of about 2 μm in those synthesized after 60 minutes. Only in cases of CaP-NP synthesized after 5 and 10 minutes, the average mean hydrodynamic radius met the features required for use in the invention.

Figure 2:
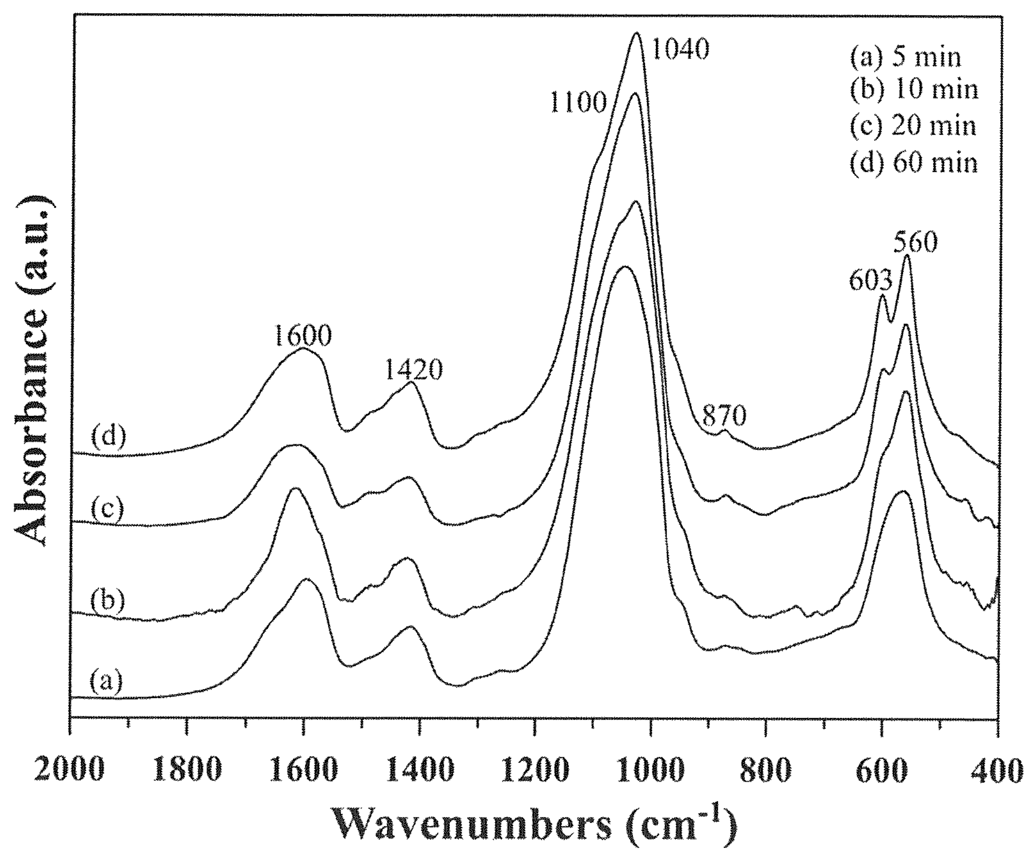
FIG. 2 shows the effects of the maturation time on the CaP-NP generated. Fourier transform infrared spectroscopy (FTIR) of the CaP-NP at different synthesis times and using a concentration of citrate equal to 80 mM. Peaks at 560 and 603 correlate the degree of crystallinity.

The degree of crystallinity was calculated from the FT-IR spectra in FIG. 2 by assessing the splitting factor (SF) (Weiner S. and Bar-Yosef O. (1990). States of preservation of bones from prehistoric sites in the Near East: a survey. Journal of Archaeological Science 17, 187-196.). The SF was measured by the sum of the peak heights of the stretching of phosphates at 603 and 560 $cm^{-1}$ divided by the height of the valley point between them. All heights were measured above a baseline drawn from approximately 780 to 495 $cm^{-1}$. The higher the SF, the higher the crystallinity of the material, as shown in table 1 below. The SF of CaP-NP after 5 minutes of crystallization was not measurable since the bands of phosphates at 603 and 560 $cm^{-1}$ were not resolved, indicating a very low degree of crystallinity. On the other hand, the SF increased with increasing crystallization time, indicating that the crystallization time affected the degree of crystallinity of the material.

TABLE 1

| Crystallization time (minutes) | Splitting factor (SF) |
|---|---|
| 5 | Unmeasurable (unresolved bands) |
| 10 | 1.76 |
| 20 | 2.16 |
| 60 | 2.25 |

With crystallization times longer than 10 minutes, the level of crystallinity finally achieved was too high, thus rendering the product not suitable for the intended application. Advantageously, the decrease of the time of degradability of CaP-NPs, allowed to have a slow release of the therapeutic/diagnostic compound, while by increasing the level of crystallinity obtained by this procedure decreased the time of degradability of CaP-NPs, thus determining a slow release of the therapeutic/diagnostic compound.

Example 1C: Effects of Step b) of the Invention

In order to remove non-reacted ions during crystallization, dialysis was used as indicated in example 1A.

Figure 3:
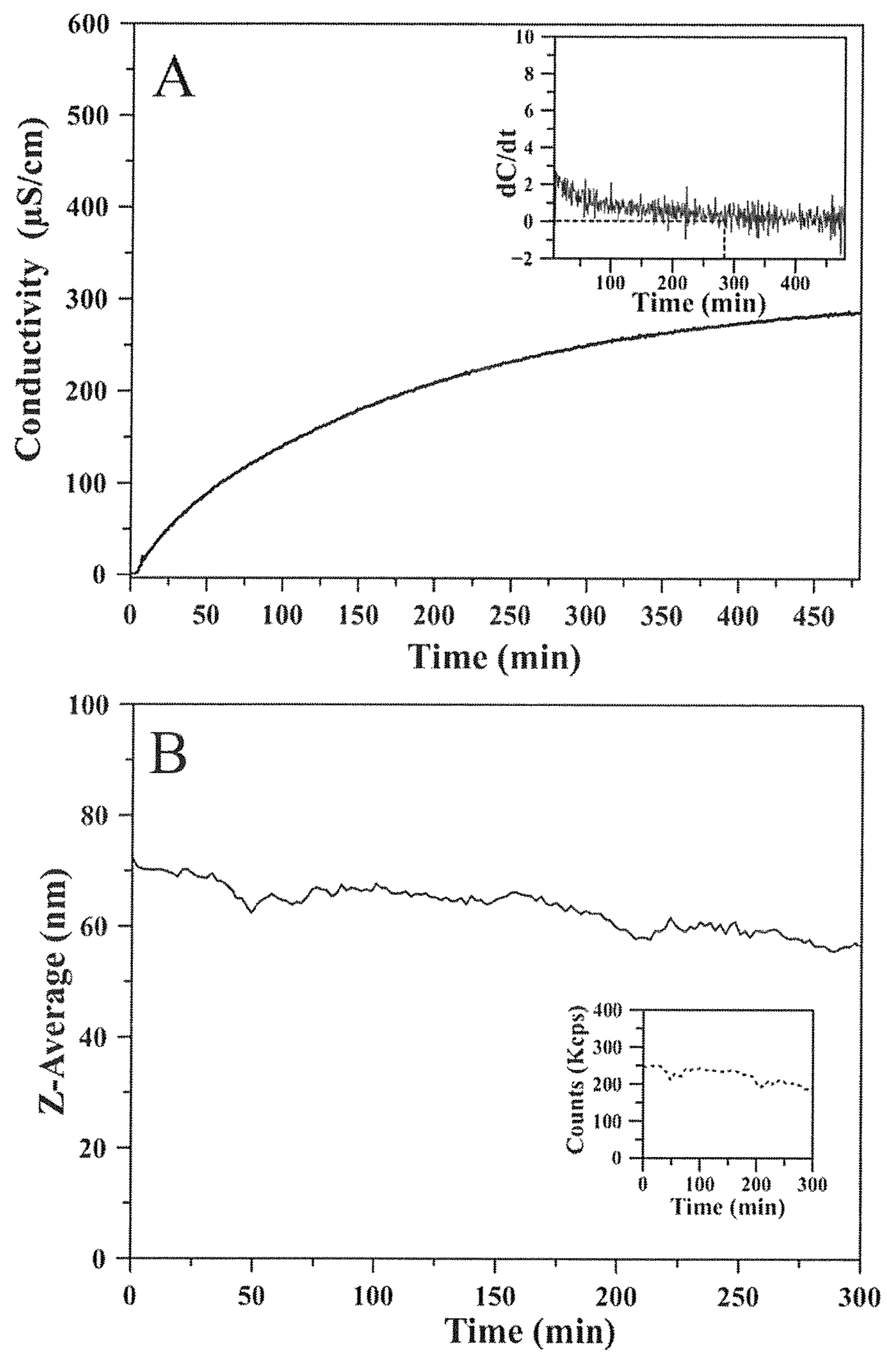
FIG. 3 shows (A) the conductivity of the of the dialysate solution as a function of time and (B) the stability of the CaP-NP in solution after 6 hours of dialysis assessed by DLS through measurements of Z-average

In order to test the optimal time so that all the excess ions in the reaction environment are removed by dialysis, the conductivity of the dialysis medium over time was assessed and a plateau was observed after 6 hours (FIG. 3A). The conductivity plateau reached indicated that the ion exchange from the reaction medium to the dialysis medium had ended and that most non-reacted ions had been transferred in the wash water. The ζ-potential of CaP-NP after the dialysis time was measured as shown in Table 2 below.

TABLE 2

| Dialysis time (hours) | ζ-potential (mV) |
|---|---|
| 2 | +37.0 ± 0.7 |
| 4 | −35.6 ± 0.6 |
| 6 | −39.5 ± 1.5 |

The results indicated that increasing the dialysis time decreased the average mean hydrodynamic diameter of CaP-NP, while ζ-potential remained constant. The stability of CaP-NP after 6 hours of dialysis had been confirmed by DLS (FIG. 3B). FIG. 3B shows the value of the Z-average of CaP-NP after 6 hours of dialysis as a function of time. It can be seen that no alterations in the dimensions of CaP-NP were observed up to 300 minutes, in fact the dimensional value seems to remain constant over time. The insert in FIG. 3B shows the number of photons detected per second for a period up to 300 minutes. This analysis allowed recognizing an optimal colloidal stability of CaP-NP after 6 hours of dialysis in solution, since the number of photons remained constant for 300 minutes.

Figure 4:
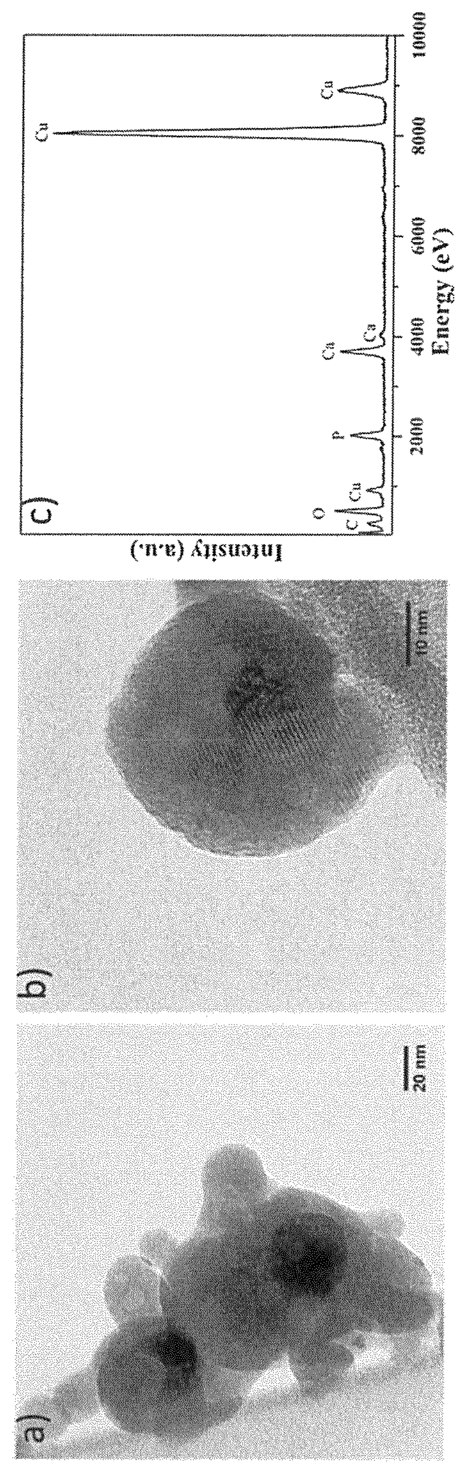
FIG. 4 shows an analysis of transmission electron microscopy (TEM) of the CaP-NP synthesized using a concentration of citrate equal to 80 mM without (A) and after 6 hours of dialysis (B); and (C) an analysis of the CaP-NP by EDX (Energy Dispersive x-ray Spectrometry) spectroscopy.

FIG. 4 shows the TEM analysis of CaP-NP without (FIG. 4A) and after 6 hours of dialysis (FIG. 4B). It can be seen that before dialysis, the CaP-NP (recognizable by the spherical dimension and by the darker color and with dimensions of about 20-30 nm in diameter) are coated with a layer of organic material that is most likely the citrate remained in solution that is not physically bound to the CaP-NP. Conversely, the CaP-NP after 6 hours of dialysis also in this case had a spheroidal morphology and dimensions of around 30-50 nm but were better defined and visibly without the surface organic part. EDX spectroscopy analyses (FIG. 4C) on selected area were conducted on the CaP-NP after 6 hours of dialysis and they showed the signals due to elements Ca, P (in addition to those of Cu due to the sample holder and those of O and C due to both the sample and to the external environment), confirming that the CaP-NP mainly consist of calcium phosphate and no other phase is formed during dialysis.

Example 2: Tagging of the CaP-NP of the Invention

In order to assess the cellular internalization of NP obtained from example 1A, the NP were marked with fluorescein isothiocyanate (FITC).

CaP-NPs were prepared as in example 1A but with the inclusion of the FITC compound as described hereinafter.

A solution containing: 12.5 volumes of a solution of $CaCl_2$ (10-50 mM) and $Na_3$ ($C_6H_5O_7$) (40-200 mM), 1 volume of a solution of NaOH (0.1-0.5 M) and 12.5 volumes of a solution of $Na_2HPO_4$ (12-60 mM) was prepared and then placed in a water bath at 37° C. for 5 min. To remove non-reacted reagents, the solution of CaP-NP was subjected to dialysis for 6 hours in a cellulose dialysis membrane having a cutoff of 3500 Dalton and immersed in 400 ml of bidistilled water. A suspension of CaP-NP was then obtained.

Initially, FITC was conjugated with 3-aminopropyltriethoxysilane (APTS) (hereinafter, this mixture is referred to as FITC-APTS) following this protocol: FITC (0.025 mmol) and APTES (0.25 mmol) were added to 10 mL of ethanol and kept under stirring at 600 rpm in the dark for 24 hours.

100 μL of FITC-APTS, 100 μL of ammonium hydroxide (28 wt % NH3 in H2O) and 100 μL of etraethyl orthosilicate (TEOS) were then added to the aqueous suspension of CaP-NP. This suspension was kept under stirring at 600 rpm in the dark for 24 hours. The CaP-NP-FITC were washed 3 times with bidistilled water by centrifugation to remove the non-reacted FITC.

The CaP-NP-FITCs obtained were therefore used in the subsequent examples for the assessment of the biological activity.

Example 3: Preparation of CaP-NP Encapsulating microRNA (Example of Therapeutic Compound) (CaP-NP-miR)

The preparation of CaP-NP with microRNA encapsulation was carried out following in detail the preparation protocol as described in example 1A implemented by inclusion of the microRNA compound as described hereinafter. The microRNA, corresponding to the microRNAs miR-133, is a synthetic nucleotide sequence (synthesized by IBA, Germany).

A solution containing: 12.5 volumes of a solution of $CaCl_2$ (10-50 mM) and $Na_3$ ($C_6H_5O_7$) (40-200 mM), 1 volume of a solution of NaOH (0.1-0.5 M), 12.5 volumes of a solution of $Na_2HPO_4$ (12-60 mM) containing different concentrations of microRNA (0.5-10). The solution was then placed in a water bath at 37° C. for 5 min. Subsequently, the suspension was dialyzed for 6 hours and stored at 4° C. The resulting CaP-NP encapsulating miR-133 (hereinafter briefly referred to as CaP-NP-miR) were then analyzed by dimensions, ζ-potential and morphology.

The solution was then recovered and stored in a refrigerator at 4° C.

The final concentration of the aqueous suspension of CaP-NP-miR was in the range from 60 to 300 μg/ml (see Table 3).

The characterization of CaP-NP-miR particles is shown in table 3 below.

TABLE 3

| Initial concentration of miRNA (μg ml$^{-1}$) | Z-average (nm) | ζ-potential (mV) | Polydispersity index (pdI) |
|---|---|---|---|
| 1 | 156 ± 6 | −29.6 ± 2.6 | 0.33 ± 0.10 |
| 5 | 199 ± 11 | −36.6 ± 1.6 | 0.29 ± 0.05 |
| 10 | 225 ± 6 | −32.1 ± 3.0 | 0.17 ± 0.01 |

Figure 5:
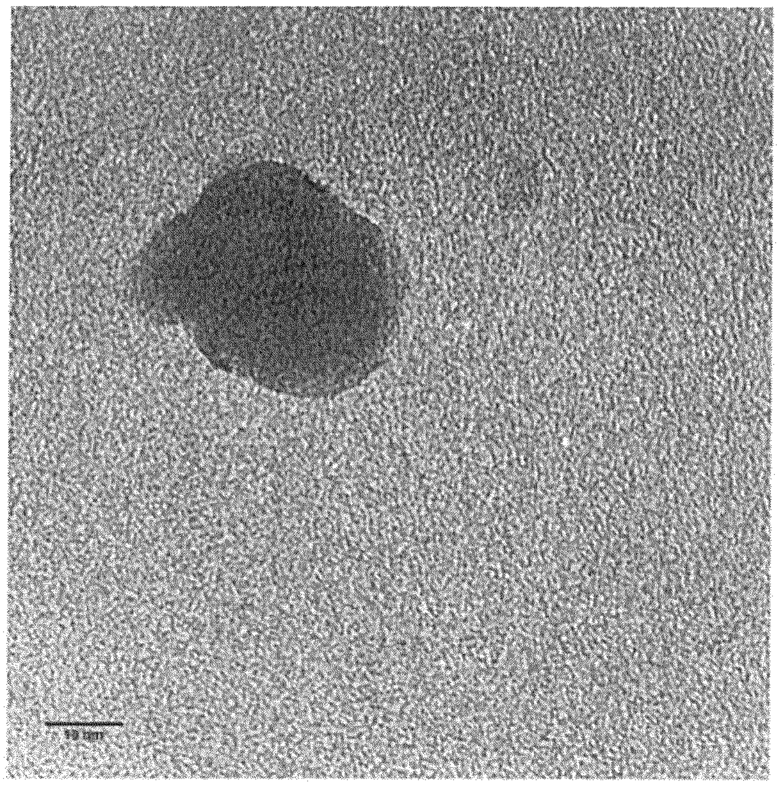
FIG. 5 shows an analysis of transmission electron microscopy (TEM) of the CaP-NP-miR using an initial concentration of miR equal to 10 μg/ml.

The suspension of CaP-NP-miR was analyzed by DLS, revealing a Z-average of particles in the range 150-231 nm and ζ-potential in the range from −41.0 mV to −27.0 mV. Moreover, the pdI had values close to 0 indicating a narrow distribution of the sample dimensions. The TEM analysis of the product of the invention, i.e. of the CaP-NP-miR, revealed that the size of every single particle was about 50 nm (FIG. 5).

Example 4: Assessment of the Amount of miR-133 Encapsulated in the CaP-NP-miR of the Invention in Example 3

In order to assess the exact amount of miR-133 encapsulated in the CaP-NP-miR, a quantitative PCR (qPCR) measurement was carried out on total nucleic acids extracted from CaP-NP-miR. From three preparations of CaP-NP-miR as described in example 3 and using different concentrations of miR-133 (2, 25, 50 μg) used during synthesis, 500 μl of a solution of CaP-NP-miR were used for the extraction of RNA through Purezol reagent (Promega). A total of 40 ng of RNA extracted for each preparation of CaP-NP-miR was then reverse transcribed using a universal cDNA Synthesis II kit (Exiqon). Then, 1/40 of the reverse transcription reaction was used for the subsequent miR-133-specific qPCR, which was carried out in triplicate on a VIIa™ 7 Real-Time PCR System (Applied Biosystem) using SYBR® Select Master Mix (Invitrogen). The exact amount of miR-133 was then determined using an absolute quantification method using serial dilutions of a cDNA derived from a known amount of synthetic oligo of miR-133 (1:10 dilution from a starting point of 40 fentomoles). The amount of miR-133 bound to the CaP-NP was estimated by tracing the Ct derived on the linear standard curve. The amount of miR-133a bound to the CaP-NP is shown in table 4. The results show that more than 50% of the microRNA used during the reaction had been encapsulated within the CaP-NP.

TABLE 4

| Preparation of CaP-NP-miR | miR-133 used in the synthesis (μg) | miR-133 encapsulated to the CaP-NP-miR (μg) |
|---|---|---|
| 1 | 5 | 2.6 |
| 2 | 25 | 20.2 |
| 3 | 50 | 41.2 |

Example 5: In Vitro Assessment of CaP-NP and Toxicity

Figure 6:
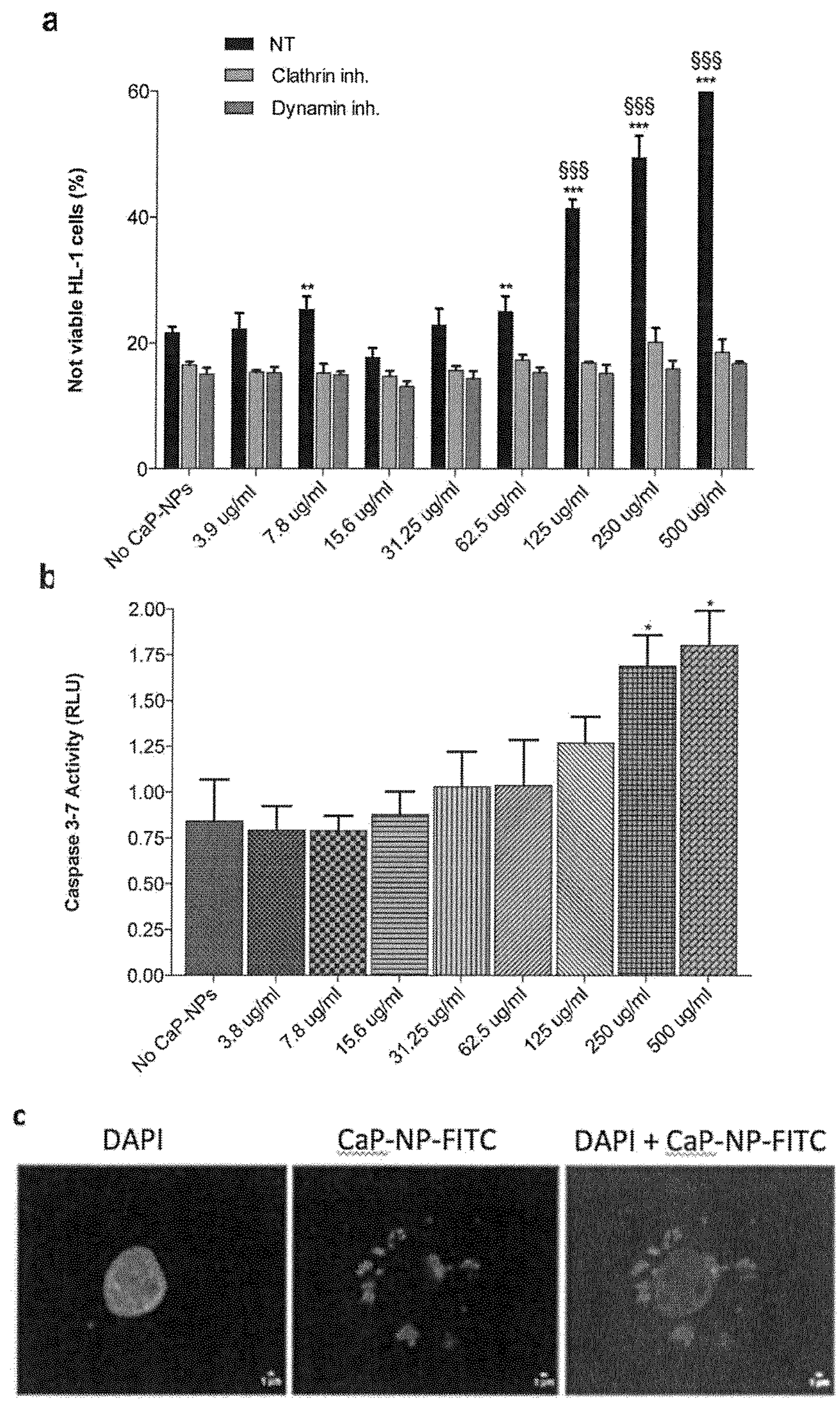
FIG. 6 shows (A) an assessment of cellular cytotoxicity analyzed by exclusion assay with trypan blue, a dye able to selectively mark only dead cells. Clathrin or dynamin inhibitors were used to highlight the endocytotic processes involved in the internalization of the CaP-NP. (B) Assessment of the cell apoptosis levels analyzed by caspase 3-7 assay. (C) Fluorescence image analyzed by confocal microscopy of HL-1 cells treated with CaP-NP-FITC. The CaP-NP-FITC signal identifies the internalization of CaP-NP-FITC in intracellular compartments. DAPI=nucleus.
Figure 7:
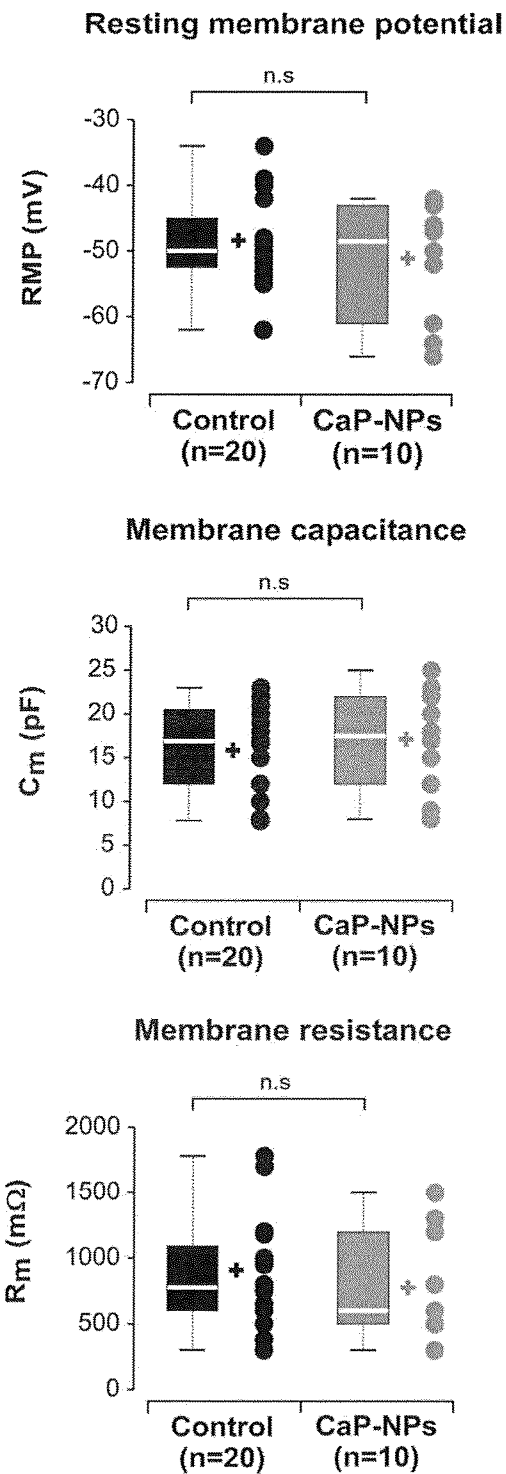
FIG. 7 shows the effects of the CaP-NP on the electrophysiology of HL-1 after 24 hours of exposure of 20 μg/mL CaP-NP. In particular, it shows box-plot of the passive properties [resting membrane potential (top), membrane capacitance (middle) and membrane resistance (bottom)] for HL-1 cells unexposed (black) and exposed (grey) to 20 μg/ml CaP-NPs.
Figure 8:
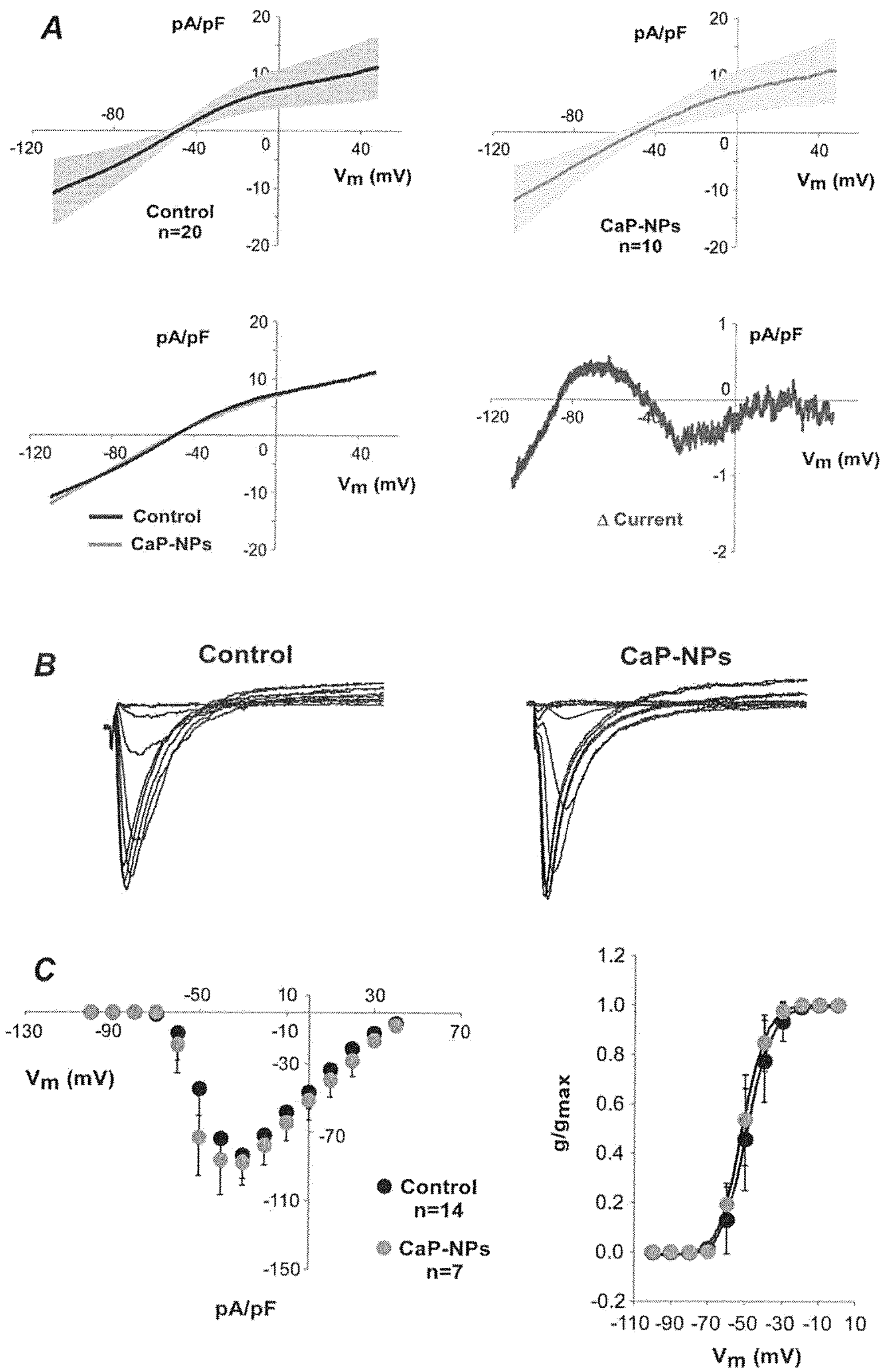
FIG. 8 shows the effects of the CaP-NP on the electrophysiology of HL-1 after 24 hours of exposure of 20 μg/mL CaP-NP. In particular, it shows (A) I-V curves obtained with ramp protocols in control (left, black: mean+SD; SD shown as a band) and exposed conditions (right, grey) HL-1 cells. Bottom row. Superimposition of the two curves (left) and average difference net membrane current curve (right). (B) Representative sodium current traces for both conditions. Bottom. Peak sodium currents I-Vs and voltage-dependencies of sodium channel activation (g/gmax, right) for control (black) and exposed (grey) HL-1 cells.
Figure 9:
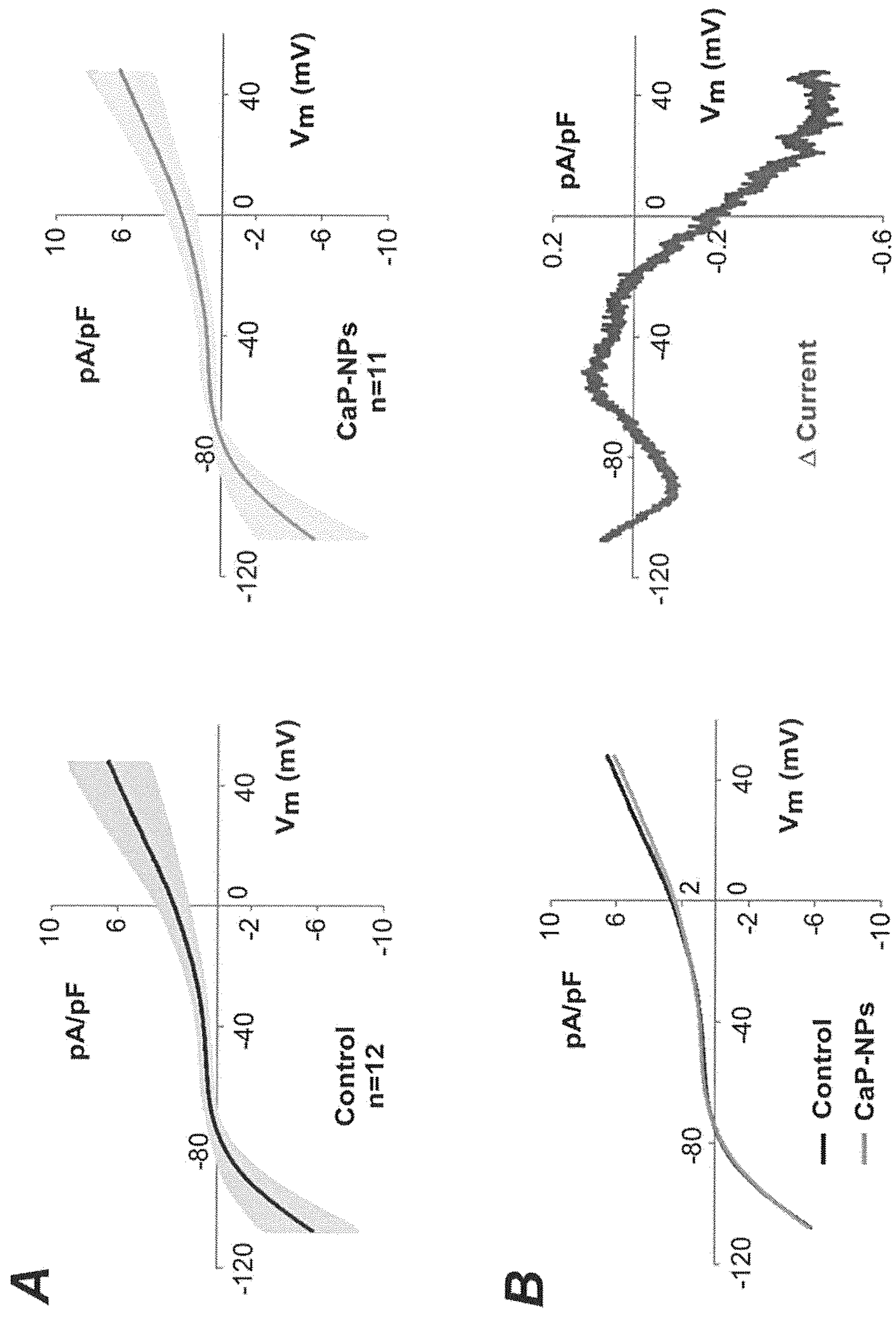
FIG. 9 shows the effects of the CaP-NP on the electrophysiology ventricular cardiomyocytes of adult mice after 5 hours of exposure of 20 μg/mL CaP-NP. In particular, (A)

CaP-NPs obtained in example 1A were tested in vitro for biocompatibility and toxicity, exposing the cardiac cell line HL-1 to increasing doses of CaP-NPs (0-500 ug/ml). As a first step, an assessment of cytotoxicity was carried out by an exclusion assay with trypan blue, a dye able to selectively mark only dead cells. As shown in FIG. 6A, the HL-1 line tolerated the administration of the amounts tested while an increase in the cellular mortality was only observed at high doses (>125 ug/ml). Subsequently, a caspase-3-7 assay was used for the assessment of any apoptotic responses induced after administration of CaP-NP. As shown in FIG. 6B, significant differences in terms of apoptotic activity were only observed at high concentrations of CaP-NP 250 ug/ml. Therefore, both assays elected the CaP-NP as a potential carrier for the internalization of the compounds of interest to the myocardium.

Example 6: Assessment of the Internalization of CaP-NP

In order to assess the cellular internalization of CaP-NP, we exposed HL-1 cells to a concentration of 20 μg/ml CaP-NP-FITC of example 2 and carried out a confocal microscopy analysis 24 hours after administration. As shown in FIG. 6C, a clear internalization of CaP-NP-FITC in distinct intracellular vesicular compartments was obtained. In order to determine whether this internalization was actually due to active endocytosis mechanisms, clathrin- or dynamin-specific inhibitors were used, proteins involved in the invagination and endocytosis of the plasma membrane. Therefore, HL-1 cells were pre-treated with these inhibitors and then exposed to increasing concentrations of CaP-NP. As shown in FIG. 6A, the clathrin/dynamin-mediated endocytosis inhibition significantly reduced cellular toxicity (in exclusion assay with trypan blue) induced by the CaP-NP at all doses, thus reflecting an inhibition of the cellular absorption of CaP-NP.

Example 7: In Vitro Assessment of CaP-NP and Electrophysiological Properties

One of the main problems in the use of calcium-based nanoparticles on excitable cells such as cardiomyocytes is the potential effect on the electrophysiological properties. We therefore studied the biophysical properties of two cell types (the HL-1 and adult mouse ventricular cardiomyocytes). Initially, we analyzed the characteristics of the action potential (AP) in HL-1 cells following the acute and chronic administration of 20 μg/ml of CaP-NP of example 1A. Specifically, 24 hours after administration, the HL-1 were used for experiments in chronic (24 hour incubation with CaP-NP) while mouse cardiomyocytes for those in acute (4 hour incubation with CaP-NP). Both in chronic and acute conditions, the electrophysiological experiments, carried out with the patch-clamp technique in whole-cell configuration, did not show any significant difference between treated and control samples both as regards the biophysical properties of resting cells and for the action potential characteristics obtained following above-threshold electrical stimulation (FIG. 7-11). It was thus seen that the parameters that define the electric phenotype of these cells and which impart the typical characteristics of excitability thereto, such as the membrane potential (Vm), membrane capacity (Cm), membrane resistance (Rm), action potential threshold (AP), AP width (APA), maximum ascent rate of AP ($dV/dT_{max}$) and duration of AP (APD), were not significantly altered following administration of CaP-NP at the above concentrations. Also the analyses, again with patch-clamp technique, of the main ionic currents normally present in the two cell types studied at the basis of the typical AP characteristic of cardiac cells (potassium, sodium and calcium currents) showed no significant differences between control and treated with CaP-NP in both chronic and acute conditions).

Finally, an assessment of the cytosolic changes in calcium levels (calcium transient) reflecting the cyclical changes in calcium upon the alternation of the systolic/diastolic phases of cardiomyocytes was carried out. As shown in FIG. 12, no significant alteration was highlighted between the different conditions.

In conclusion, the above data show that the CaP-NP effectively entered the intracellular cytoplasmic space without altering the physiological properties of cardiomyocyte cells.

Example 8: Effects of CaP-NP with Encapsulated Diagnostic/Therapeutic Compounds

The cellular internalization of CaP-NP with a synthetic duplex oligo mimicking the miR-133 (used in example 3) encapsulated therein was assessed. Therefore, the product of the invention was prepared as CaP-NP conjugated to miR-133 (CaP-NP-miR) following example 3 and using a solution of synthetic miR-133. miR133, a muscle-specific microRNA, which was known to be a negative beta-adrenergic receptor modulator.

The internalization of the compound of the invention was then confirmed by qPCR carried out on total RNA extracted from cells previously treated with incremental doses of CaP-NP-miR. As shown in FIG. 13, each treatment with increasing doses of CaP-NP-miR corresponded to incremental values of intracellular miR-133.

These data provided evidence that the miR-133 compound, encapsulated in the CaP-NP-miR particles, was actually actively internalized into cells. Therefore, such evidence supports the use of CaP-NP for an efficient intracellular delivery of therapeutic/diagnostic compounds.

Example 9: In Vivo Assessment of Potential Adverse Effects on Cardiac Function Following Administration of the Product of the Invention In order to assess whether the CaP-NP produced in example 1A) successfully reached the myocardium without affecting the heart activity, a test in vivo was conducted on adult rat. The animals, anesthetized as described in document Rossi et al. AJP 2008, were administered by tracheal route a saline as such (CTL) or containing CaP-NP at a concentration of 3 mg per Kg of body weight of the animal. 4 hours after treatment, the animals were subjected to electrophysiological analysis. The electrograms obtained from an electrode device placed on the epicardial surface are shown in FIG. 15. As shown in FIG. 14 and in table 5 below, the electrograms showed no qualitative differences between the two experimental groups in terms of P, PQ, QRS, QT, ERP, RR.

TABLE 5

Electrograms of animals treated with saline as such (CTL) or containing the CaP-NP.

| | Chronaxie (mA) | P wave duration (ms) | PQ interval (ms) | QT interval (ms) | RR interval (ms) | QRS Duration (ms) |
|---|---|---|---|---|---|---|
| CTL | 1.2 ± 0.2 | 27.5 ± 0.4 | 32.3 ± 0.5 | 41.8 ± 0.7 | 262.6 ± 2.8 | 15.6 ± 0.2 |
| CaP-NP of the invention | 0.9 ± 0.2 | 29.6 ± 0.5 | 33.0 ± 0.5 | 37.8 ± 0.6 | 285.2 ± 2.5 | 14.9 ± 0.1 |

Therefore, the non-alteration of the heart ECG parameters confirmed that an administration of CaP-NP did not lead to any form of modulation of cardiac excitability, thus anticipating the physiological cardiac tolerance to the product of the invention and the overcoming of the technical problem anticipated by the use of nanoparticles of a different nature.

Finally, in order to assess the actual delivery of the CaP-NP to the heart, rats were exposed to a single intratracheal administration of a saline solution containing the CaP-NP-FITC (fluorescein isothiocyanate) (3 mg/Kg) prepared as shown in example 1B. 4 hours after administration, the heart was isolated and analyzed by two-photon microscopy. Surprisingly, a widespread distribution of the product of the invention was observed in the heart tissue, with particular abundance in the left ventricle, thus suggesting that the product of the invention indeed reached the heart through tracheal administration. This result is represented by the cardiac tissue fluorescence image as shown in FIG. 15. Moreover, a multiple-administration approach (once daily repeated three times and every other day) led to an increase in fluorescence mainly in the left heart ventricular chamber, suggesting that the cardiac bioavailability related to the heart tissue followed a dose-dependent increase.

Example 10: Therapeutic Potential of the Product of the Invention in a Mouse Model of Cardiac Disease (Diabetic Cardiomyopathy)

To further explore the potential therapeutic application, CaP-NPs were produced as in example 1A) implemented by inclusion of the mimetic peptide (MP) as described for the microRNA in example 3. MP is a short 9aa peptide (synthesized by Genescript, USA) that falls in a novel class of positive inotropes. By acting via unconventional mechanisms (i.e. normalization of cell surface density of the voltage-dependent L-Type calcium channel, which is the trigger element leading to the calcium-dependent systolic contraction, and without altering the channel gating properties), MP restores the force of the heartbeat in condition of cardiac dysfunciton where LTCC density, and consequently cardiac contractility, is downregulated (i.e. diabetic cardiomyopathy, DM). To induce DM, mice were injected with streptozotocin (STZ), a compound that is toxic for the insulin-producing beta cells of the pancreas. Intriguingly, 10 days of an inhalation treatment of DM mice with MP-CaP-NP completely restored cardiac function, while no effects were obtained when MP alone or scramble-CaP-NP (CaP-NP-HA) were administered (FIG. 16A). In addition, functional analyses of cardiomyocytes isolated from the same treated mice revealed that the MP-CaP-NP restored calcium current (Ica) (FIG. 16B).

The invention claimed is:

1. A process for the preparation of a product comprising one or more nanoparticles of calcium phosphate (CaP-NP) with a negative surface charge having a potential in the range from −41.0 mV to −27.0 mV, comprising the steps of:

a) maintaining a mixture having a pH in the range from 7 to 10 and comprising an aqueous solution of calcium chloride, an aqueous solution of phosphate and a solution of citrate ions at a temperature in the range from 20° C. to 40° C. for a time in the range from 5 minutes to 10 minutes;

b) removing non-reacted ions from the obtained solution of step a), thus obtaining a suspension of one or more nanoparticles of calcium phosphate (CaP-NP) free from non-reacted sodium ions;

c) recovering, from the suspension of step b), the one or more nanoparticles of calcium phosphate (CaP-NP) free from non-reacted sodium ions.

2. The process according to claim 1, wherein in the mixture of step a) an aqueous solution of one or more therapeutic/diagnostic compounds is also present.

3. The process according to claim 1, wherein the one or more nanoparticles of calcium phosphate (CaP-NP) recovered from step c) are surface functionalized with one or more therapeutic/diagnostic compounds.

4. The process according to claim 1, wherein the aqueous solution of calcium chloride in the mixture of step a) is a solution of Calcium Chloride having a molarity in the range from 20 to 200 mM.

5. The process according to claim 1, wherein the aqueous solution of phosphate in the mixture of step a) is a solution of $Na_2HPO_4$ with molarity in the range from 24 to 240 mM.

6. The process according to claim 1, wherein the temperature of step a) is in the range from 35 to 40° C.

7. The process according to claim 6, wherein the temperature of step a) is about 37° C.

8. The process according to claim 1, wherein the maintenance time of the mixture of step a) is about 5 minutes.

9. The process according to claim 1, wherein the solution of citrate ions is an aqueous solution of sodium citrate having a molarity in the range from 40 to 800 mM.

10. The process according to claim 1, wherein the mixture of step a) has a pH of about 10.

11. The process according to claim 1, wherein the step b) of removing the non-reacted ions is carried out through a dialysis membrane.

12. The process according to claim 11, wherein the dialysis membrane is a cellulose membrane having a cut-off of 3500 Dalton.

13. The process according to claim 12, wherein the removal step b), carried out with a dialysis membrane, occurs for a time from 5 to 24 hours, preferably for 6 hours.

14. The process according to claim 1, wherein the recovery step c) of the nanoparticles of calcium phosphate (CaP-NP) is carried out by freezing drying.

15. A product comprising one or more CaP-NP obtainable by the process according to claim 1, wherein the NPs have negative surface charge having ζ-potential in the range from −41.0 mV to −27.0 mV and having a splitting factor (SF) of at most 1.76.

16. The product of claim 15, wherein the one or more CaP-NP comprises/comprise one or more surface-functionalized therapeutic/diagnostic compounds.

17. The product of claim 16, wherein one or more therapeutic/diagnostic compounds are selected from the groups consisting of nucleic acids, peptides, synthetic compounds and diagnostic probes.

18. A method for the treatment of cardiovascular diseases comprising the step of administering a product of claim 16.

19. The method of claim 18, wherein the treatment is carried out through an administration route selected from inhalation administration, enteral administration, parenteral administration, intravenous administration, intraperitoneal administration, oral administration, sublingual administration, spray administration, rectal administration, intraocular administration, topical administration and transdermal administration.

20. A product comprising one or more CaP-NP obtainable by the process according to claim 1, wherein the NPs encapsulate one or more therapeutic/diagnostic compounds, have negative surface charge having ζ-potential in the range from −41.0 mV to −27.0 mV, and Z-average in the range from 150 to 231 nm.

21. The product of claim 20, wherein one or more therapeutic/diagnostic compounds are selected from the groups consisting of nucleic acids, peptides, synthetic compounds and diagnostic probes.

22. A method for the treatment of cardiovascular diseases comprising the step of administering a product of claim 20.

23. The method of claim 22, wherein the treatment is carried out through an administration route selected from inhalation administration, enteral administration, parenteral administration, intravenous administration, intraperitoneal administration, oral administration, sublingual administration, spray administration, rectal administration, intraocular administration, topical administration and transdermal administration.

24. The process according to claim 1, wherein said removing is carried out through a dialysis membrane, electrophoretic deposition, or molecular exclusion chromatography.

* * * * *